United States Patent [19]

Kidani et al.

[11] Patent Number: 4,845,124

[45] Date of Patent: Jul. 4, 1989

[54] PLATINUM (IV) COMPLEXES

[75] Inventors: Yoshinori Kidani, Mataho Kohdan Jutaku 2-718, 1, Mataho-cho 2-chome, Nishi-ku, Nagoyashi, Aichi-ken; Masahide Noji, Nagoya, both of Japan

[73] Assignee: Yoshinori Kidani, Aichi, Japan

[21] Appl. No.: 20,893

[22] Filed: Mar. 2, 1987

[30] Foreign Application Priority Data

Mar. 7, 1986 [JP] Japan .................................. 61-48625

[51] Int. Cl.$^4$ ........................ A61K 33/00; C07F 15/00
[52] U.S. Cl. .................................. 514/492; 556/137; 556/40

[58] Field of Search .................. 514/492; 556/137, 40, 556/41

[56] References Cited

U.S. PATENT DOCUMENTS 4,169,846 10/1979 Kidani et al. .................. 556/137 X
4,466,924 8/1984 Verbeek .............................. 556/137

Primary Examiner—Paul F. Shaver
Assistant Examiner—Stuart L. Hendrickson
Attorney, Agent, or Firm—Larson and Taylor

[57] ABSTRACT

New platinum (IV) complexes are now provided, which exhibit antitumor activity as shown by the tests on mouse leukemia, L-1210 cell in mice. These new platinum (IV) complexes contain 1,2-cyclohexanediamine or 2-(aminomethyl)cyclohexyl-amine as a ligand.

9 Claims, 18 Drawing Sheets

PLATINUM (IV) COMPLEXES

SUMMARY OF THE INVENTION

This invention relates to new platinum (IV) complexes which exhibit antineoplastic or antitumor activity as demonstrated by the test against mouse leukemia L-1210. The platinum (IV) complexes of this invention contains a 1,2-cyclohexanediamine or 2-(amino methyl)-cyclohexylamine as a ligand.

BACKGROUND OF THE INVENTION

In recent years, a number of platinum (II) complexes, including well-known cisplatin, have been synthetized and have been reported to have antitumor activity. We the present inventors, have synthetized some platinum (II) complexes, as disclosed, for example, in Japanese Patent Application First Publn.(KOKAI) Nos. 31648/78, 35013/80, 130992/80, 103192/81, 156416/82, 16895/82, 21697/84, 34982/85, 34983/85, 97991/85, 109521/85, Japanese Patent Application Second Publn. (KOKOKU) No. 29957/83 and Japanese Patent Application No. 196887/85, as well as U.S. Pat. Nos. 4,169,846; 4,200,583; 4,256,652; 4,255,347; 4,551,524 and U.S. patent application Ser. No. 637,463 and European Patent Nos. 1126 and 8936, European Patent Appln. Nos. 83 303659.3 and 84 305304.2.

We have also synthetized some organoplatinum (IV) complexes, as disclosed, for example, in Japanese Patent Application First Publication (KOKAI) Nos. 87295/85 and 109521/85.

Meanwhile, it is always demanded that new, antitumor platinum complexes having any more excellent properties than the known antitumor organoplatinum complexes are created and provided for uses in therapeutic treatment of tumors.

DETAILED DESCRIPTION OF THE INVENTION

Now, we have succeeded in synthetizing new organoplatinum (IV) compounds of the formula (I) given below, and have also found that these new platinum (IV) compounds now synthesized exhibit an antitumor activity, as demonstrated by the test against mouse leukemia L-1210.

According to this invention, therefore, there is provided a novel platinum (IV) complexes represented by the general formula (I)

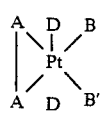   (I)

wherein the moiety

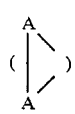

denotes a 1,2-cyclohexane-diamine ligand of the formula:

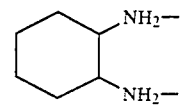

where the 1- and 2-amino groups show a configuration selected from cis-, trans-l- and trans -d- relative to the cyclohexane ring, or the moiety

denotes a 2-(aminomethyl)cyclohexylamine ligand of the formula:

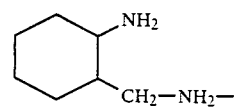

where the 1-amino group and 2-aminomethyl group show a configuration selected from cis-l-, cid-d-, trans-l- and trans-d-, or a mixture of thereof relative to the cyclohexane ring; B and B' together with the platinum atom form a ring of the formula

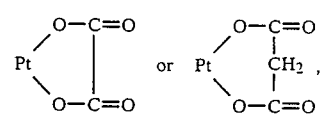

or B and B' are the same and each denotes a chlorine atom, and D denotes a chloro group a nitrate group (NO$_3$) or a hydroxy group (OH).

With the platinum (IV) complex of the formula (I) according to this invention where the moiety

is the 1,2-cyclohexane diamine (abbreviated as dach), there are 3 stereo-isomers according to the following steric structures of the 1,2-cyclohexanediamine or 1,2-diaminocyclohexane moiety.

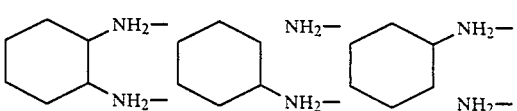

cis-dach (1R, 1S)   trans-d-dach (1S, 2S)   trans-l-dach (1R, 2R)

With the platinum (IV) complex of the formula (I) according to this invention where the moiety

is the 2-(aminomethyl) cyclohexylamine (abbreviated as amcha), there are 4 stereo-isomers according to the following steric structures of the 2-(aminomethyl)cyclohexyl amine or 1-amino-2-aminomethylcyclohexane moiety:

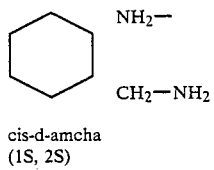

cis-d-amcha
(1S, 2S)

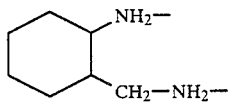

cis-l-amcha
(1R, 2R)

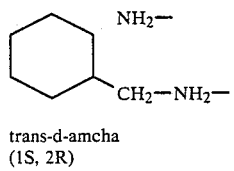

trans-d-amcha
(1S, 2R)

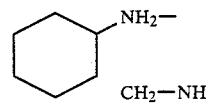

trans-l-amcha
(1R, 2S)

The platinum (IV) complexes of the formula (I) according to this invention, therefore, include some different stereo-isomers as shown above, depending on the configuration of the 1,2-cyclohexanediamine or 2-(aminomethyl) cyclohexylamine which forms a ligand to the platinum atom.

According to particular embodiments of this invention, there are provided seven types of the platinum (IV) complexes as described below:

(1) A complex of the formula (I) in which the moiety

is a ligand selected from cis-1,2-cyclohexane-diamine, trans-d 1,2-cyclohexanediamine and trans-l-1,2-cyclohexanediamine, and B, B' and D are each a chloro group.

(2) A complex of the formula (I) in which the moiety

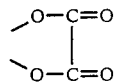

is a ligand selected from cis-1,2-cyclohexane-diamine, trans-d-1,2-cyclohexanediamine and trans-l-1-cyclohexanediamine, and B and B' are each a chloro group and D is hydroxy group (OH) or nitrate group ($NO_3$).

(3) A complex of the formula (I) in which the moiety

is a ligand selected from cis-1,2-cyclohexane-diamine, trans-d-1,2-cyclohexanediamine and trans-1,2-cyclohexanediamine, and B and B' taken together form a group of the formula $$\begin{array}{c} O-C=O \\ \phantom{XX} | \\ O-C=O \end{array}$$

and D is a hydroxy group (OH), a chloro group (Cl) or a nitrate group ($NO_3$).

(4) A complex of the formula (I) in which the moiety

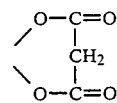

is a ligand selected from cis-1,2-cyclohexane-diamine, trans-d-1,2-cyclohexanediamine and trans-l-1,2-cyclohexanediamine, and B and B' taken together form a group of the formula $$\begin{array}{c} O-C=O \\ \phantom{XX} | \\ \phantom{XX} CH_2 \\ \phantom{XX} | \\ O-C=O \end{array}$$

and D is a hydroxy group (OH), a chloro group (Cl) or a nitrate group ($NO_3$).

(5) A complex of the formula (I) in which the moiety

is a ligand selected from cis-dl-2-(aminomethyl) cyclohexylamine and trans-dl-2-(aminomethyl)cyclohexylamine, and B, B', and D are each a chloro group.

(6) A complex of the formula (I) in which the moiety

is a ligand selected from cis-dl-2-(aminomethyl) cyclohexylamine and trans-dl-2-(aminomethyl)cyclohexylamine, and B and B' are each a chloro group, and D is a hydroxy group (OH) or a nitrate group ($NO_3$).

(7) A complex of the formula (I) in which the moiety

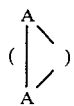

is a ligand selected from cis-dl-2-(aminomethyl) cyclohexylamine and trans-dl-2-(aminomethyl)cyclohexylamine, and B and B' taken together form a group of the formula

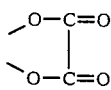

and D is a hydroxyl group (OH), a chloro group (Cl) or a nitrate group ($NO_3$).

BRIEF DESCRIPTION OF THE DRAWINGS

With reference to the attached drawings.

The platinum (IV) complex of the general formula (I) according to this invention may be prepared by one of the following two processes, (A) and (B).

Process (A)

In this process, the platinum (II) complex of the general formula (II)

wherein the moiety

B and B' are as defined above, is reacted with chlorine gas or hydrogen peroxide. The starting material, namely the compound of the general formula (II) may be prepared according to a known method, for example, the method disclosed in Japanese patent application, publication (KOKOKU) No. 41077/1985; U.S. Pat. Nos. 4,169,846 and 4,255,347.

Process (B)

In this process, such a starting compound of the general formula (I) where D is a hydroxyl group, which has been obtained in the process (A) above, is reacted with a diluted hydrochloric acid or diluted nitric acid, so that the hydroxy group for D present in the starting compound is converted into a chloro group (Cl) or nitrate group ($NO_3$), to give such compound of the formula (I) where D is Cl or $NO_3$ group.

The platinum (IV) complexes according to this invention thus obtained can be identified by their infrared absorption spectra as shown in FIGS. 1 to 18 of the attached drawings. The method for the identification of the compounds is explained below.

All the platinum (IV) complexes according to this invention commonly exhibit IR absorption peaks due to the carrier ligand present in the complexes, namely, IR absorption peaks at 3200 to 3100 cm$^{-1}$ due to $\nu NH_2$ at 2900 cm$^{-1}$ due to $\nu CH$ and at 1600 cm$^{-1}$ or thereabout due to $\nu NH_2$.

Figure 1:
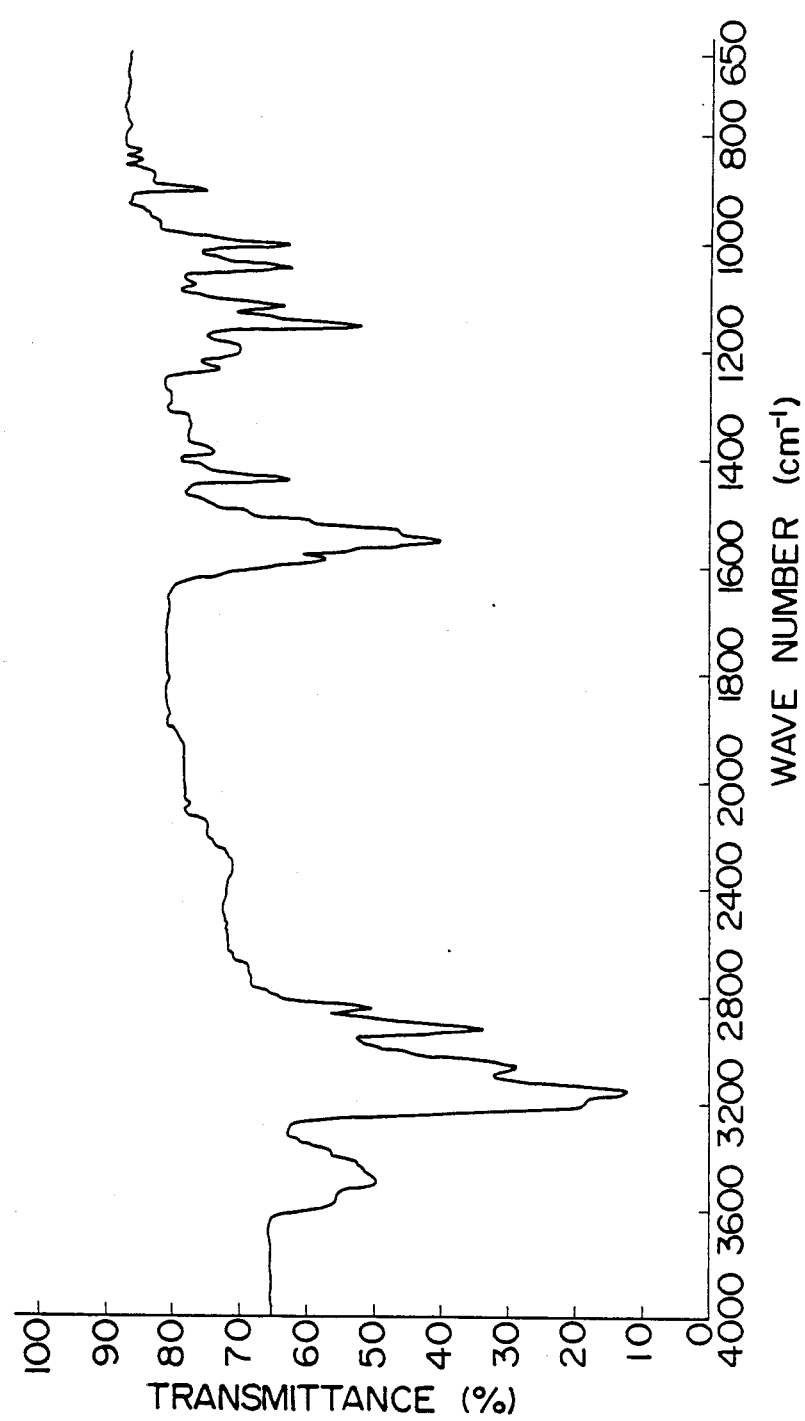
FIG. 1 is infrared absorption spectrum (KBr) of tetrachloro (trans-l-dach) platinum (IV) according to this invention.
Figure 2:
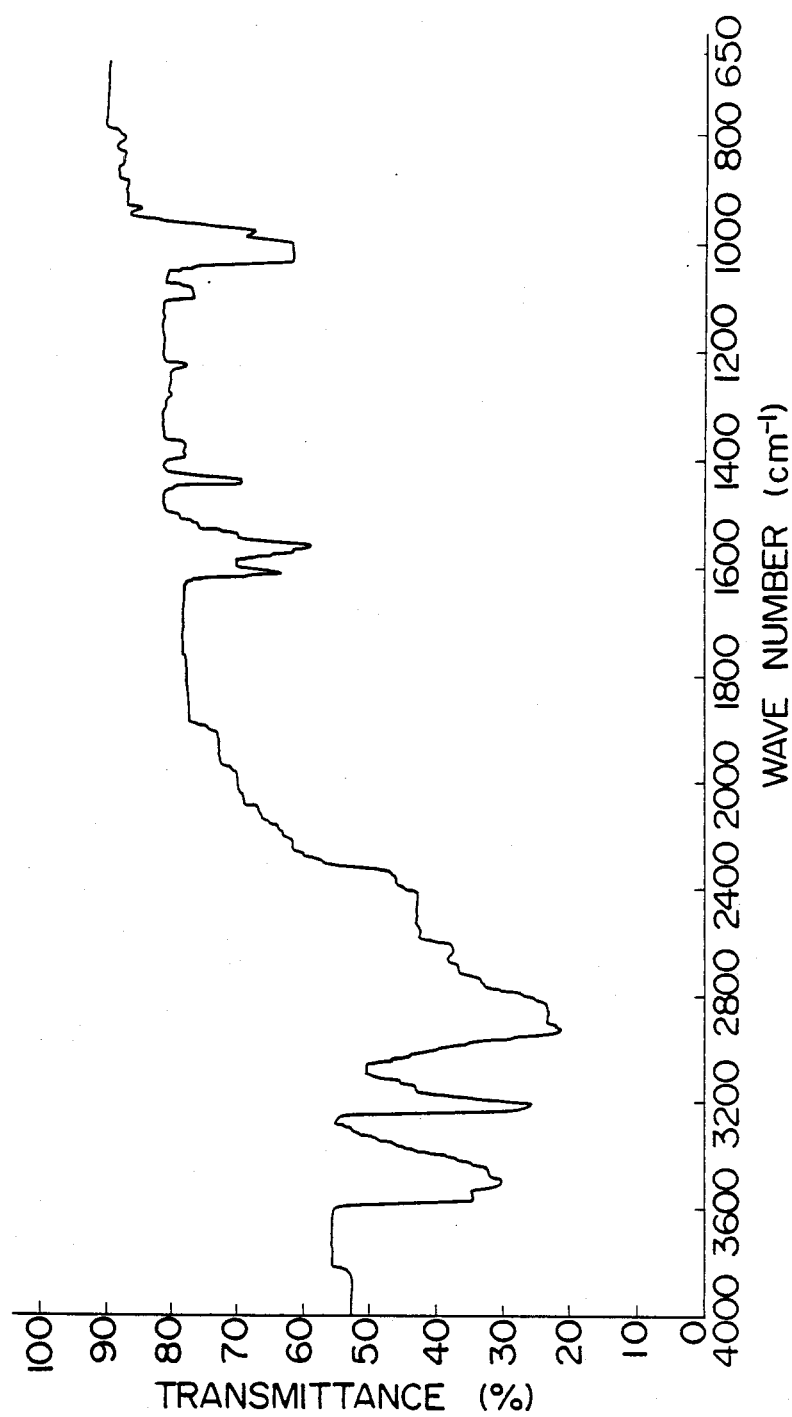
FIG. 2 is infrared absorption spectrum (KBr) of trans(OH)-dichloro-dihydroxo(cis-dach) platinum (IV) according to this invention.
Figure 3:
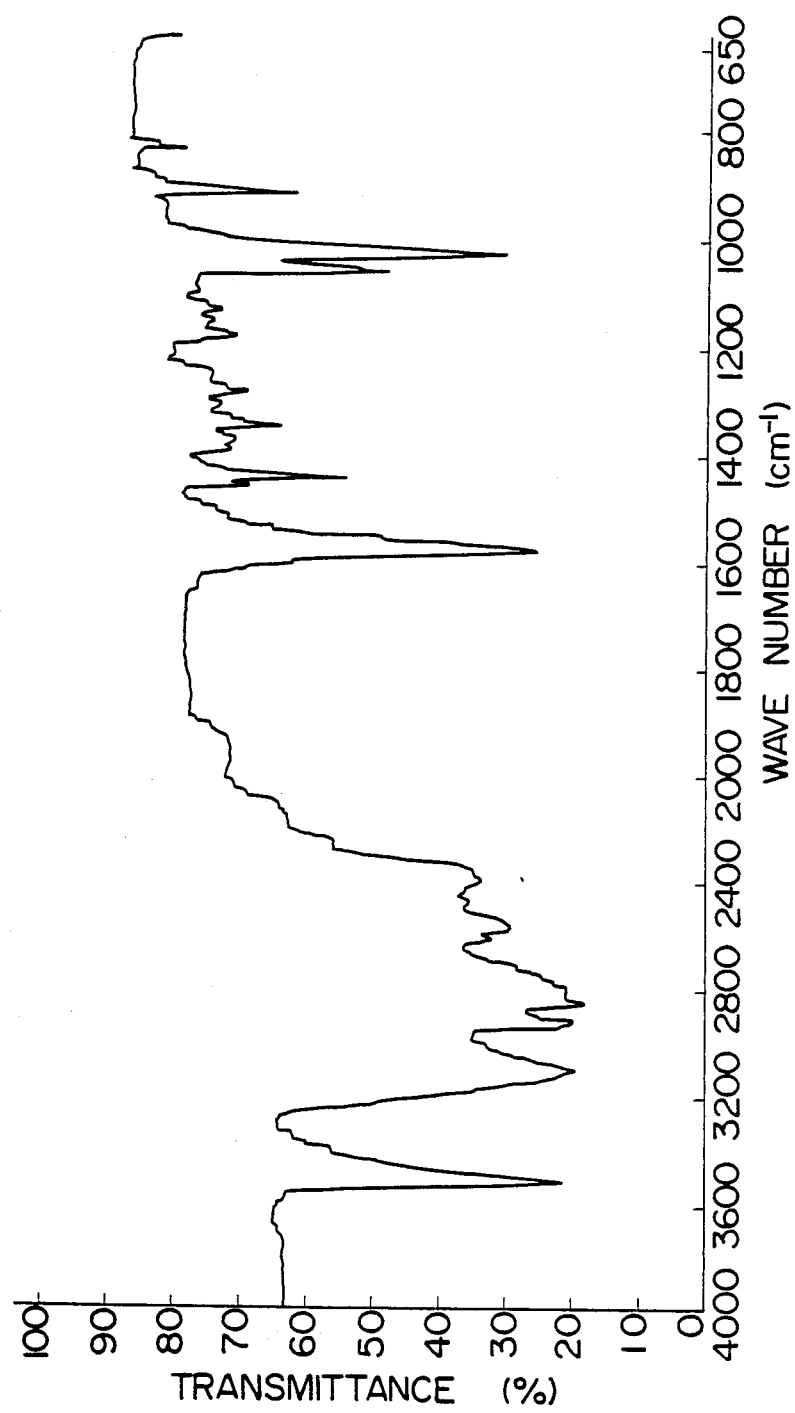
FIG. 3 is infrared absorption spectrum (KBr) of trans(OH)-dichloro-dihydroxo(trans-l-dach) platinum (IV) according to this invention.
Figure 13:
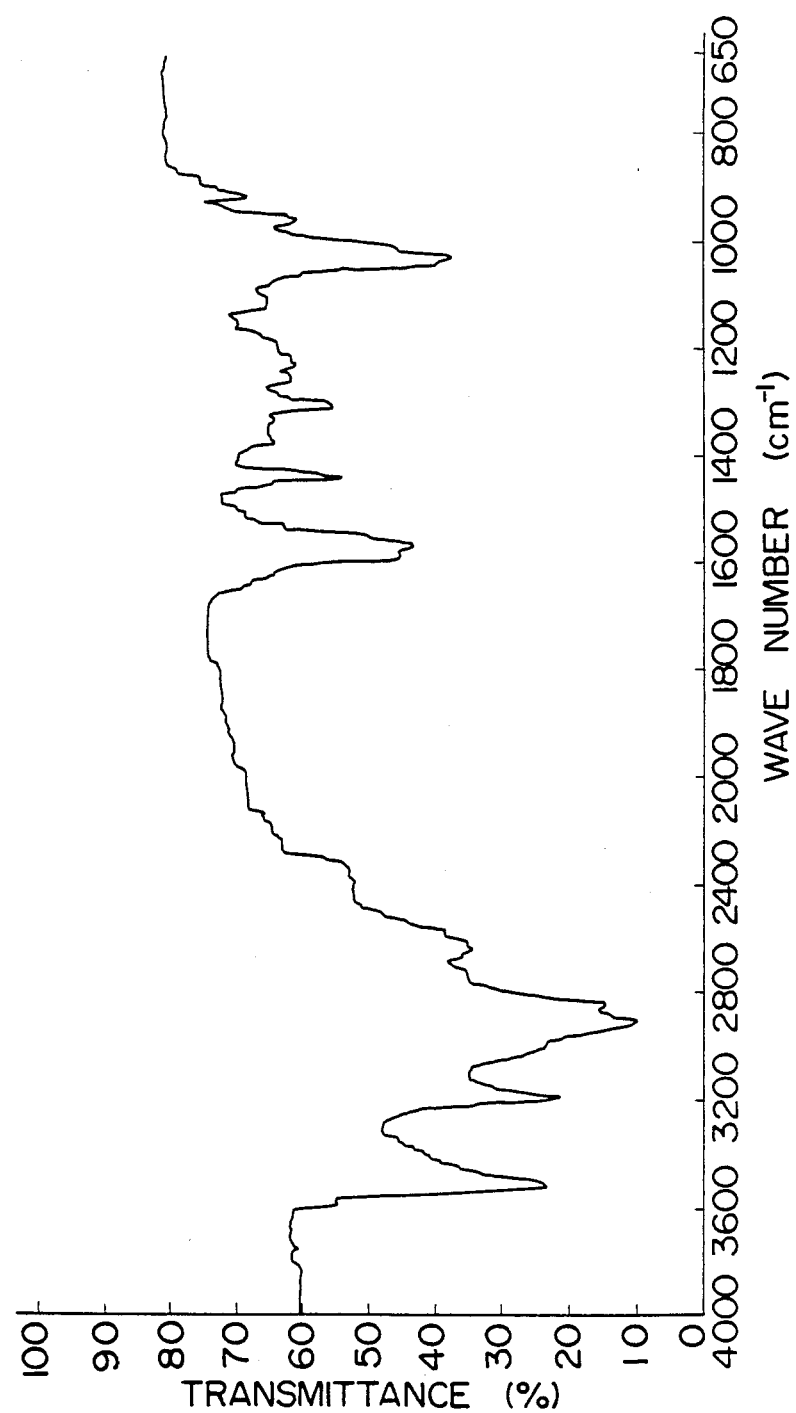
FIG. 13 is infrared absorption spectrum (KBr) of trans(OH)-dichloro-dihydroxo(cis-dl-amcha) platinum (IV) according to this invention.
Figure 14:
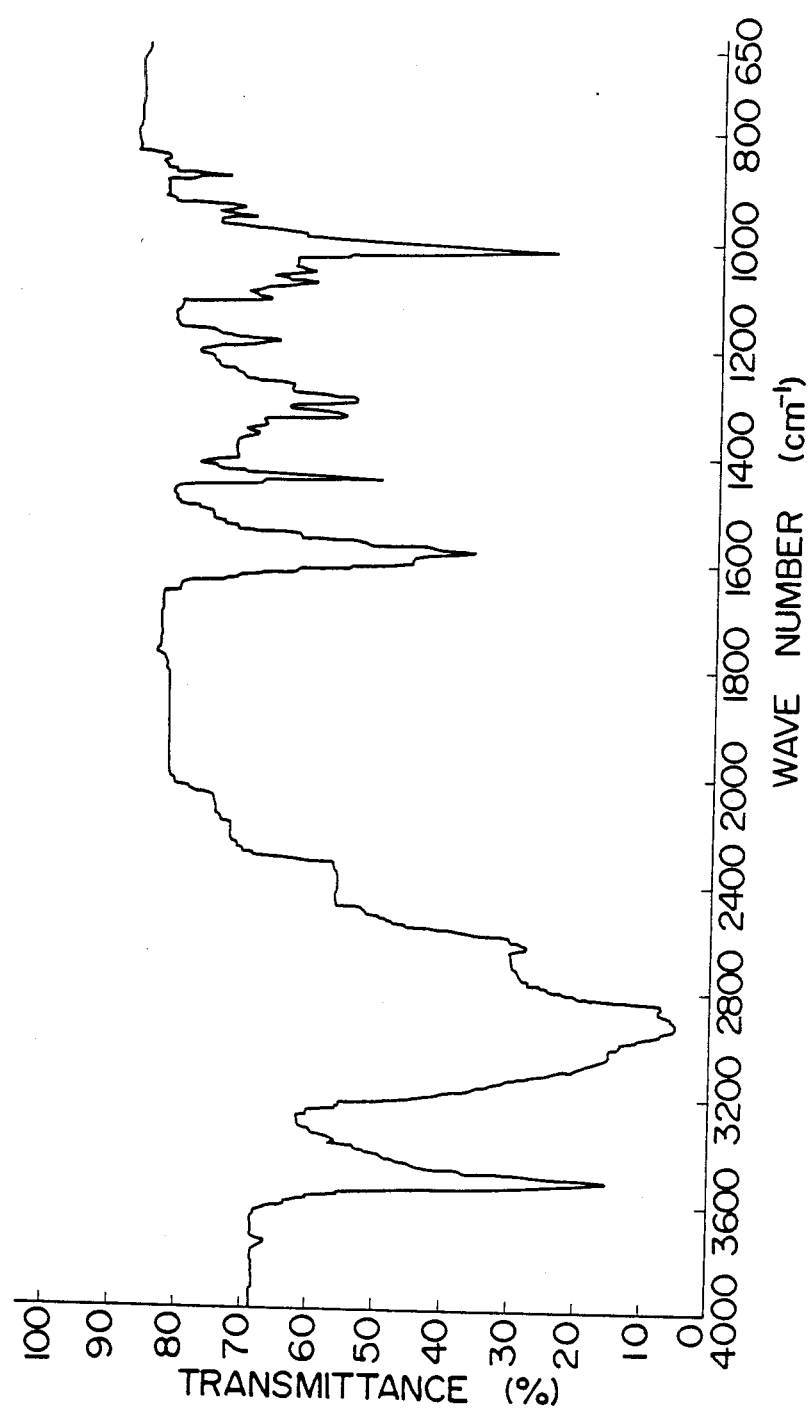
FIG. 14 is infrared absorption spectrum (KBr) of trans(OH)-dichloro-dihydroxo(trans-dl-amcha) platinum (IV) according to this invention.

By checking the shift of the characteristic infrared absorption peak as caused by the conversion of the leaving groups (D) in a particular platinum (IV) complex, this platinum (IV) complex can be identified about what is the configuration of the leaving groups relative to the platinum (IV) atoms as illustrated below:

Trans(OH)-dichloro-dihydroxo(dach) platinum (IV) and trans(OH)-dichloro-dihydroxo(amcha) platinum (IV) exhibit an IR absorption peak at 3500 cm$^{-1}$ due to νOH, as shown in FIG. 2, FIG. 3 and FIG. 13 of the attached drawings.

Figure 4:
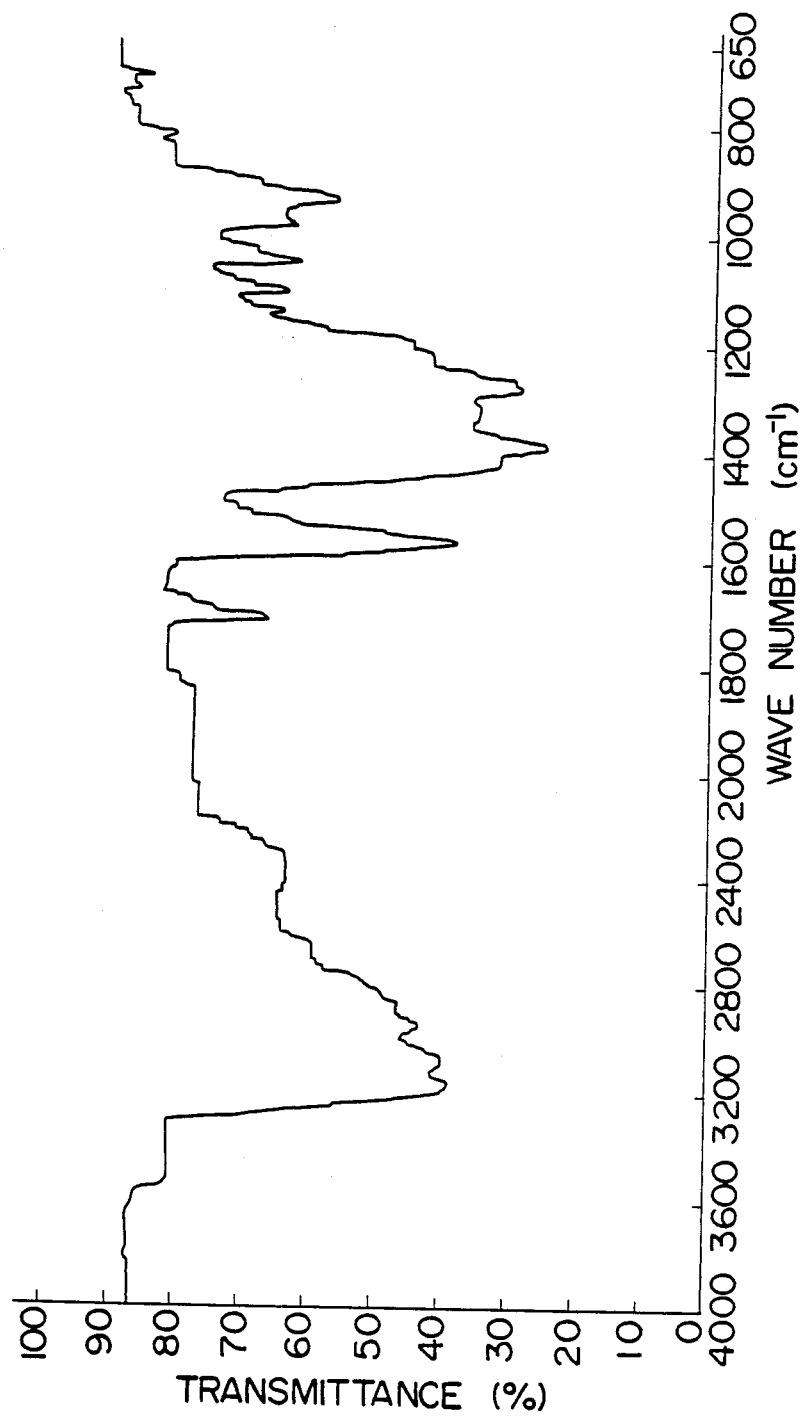
FIG. 4 is infrared absorption spectrum (KBr) of trans($NO_3$)-dichloro-dinitrato(cis-dach) platinum (IV) according to this invention.
Figure 5:
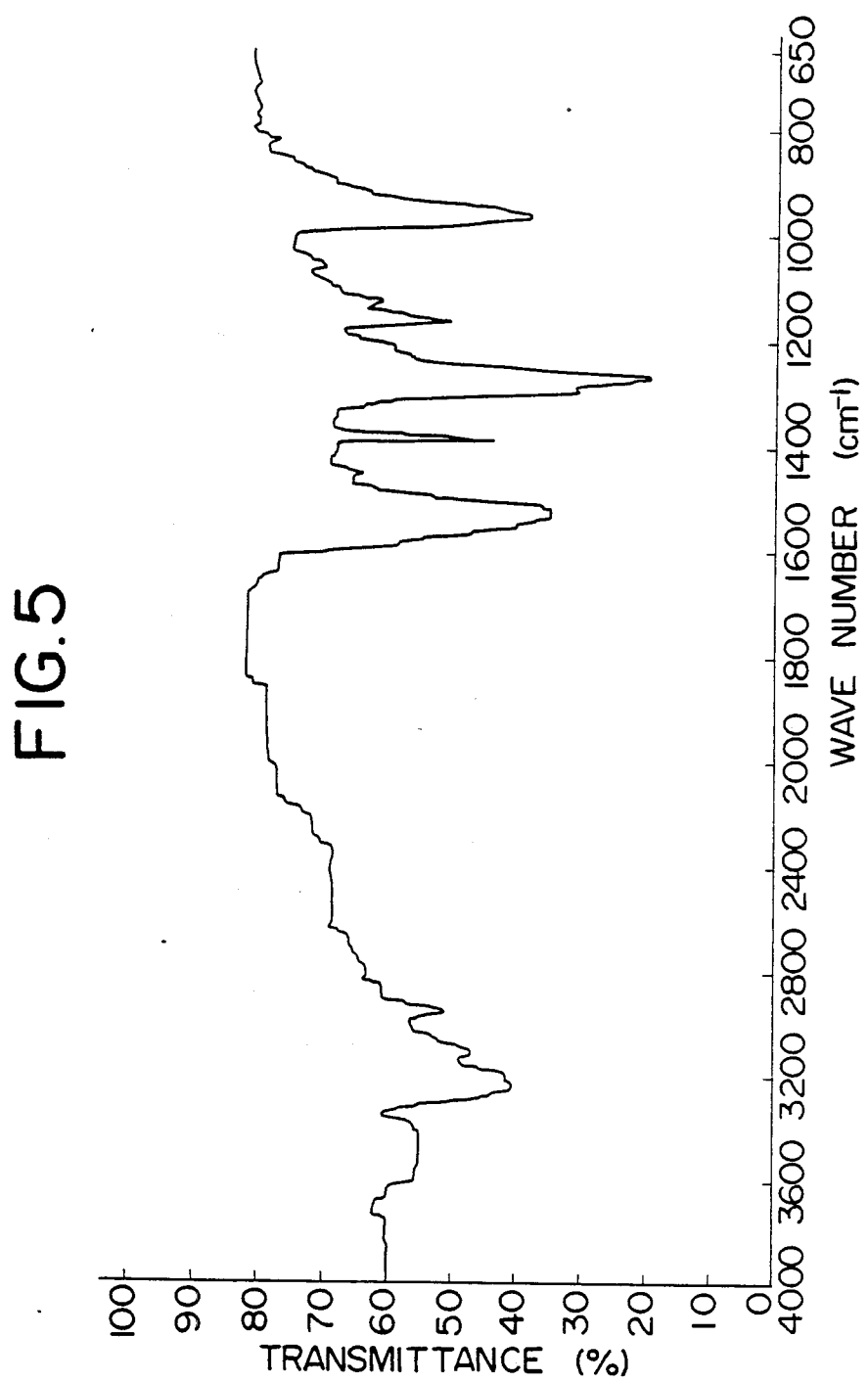
FIG. 5 is infrared absorption spectrum (KBr) of trans($NO_3$)-dichloro-dinitrato(trans-l-dach) platinum (IV) according to this invention.

Trans(NO₃)-dichloro-dinitrato(dach) platinum (IV) and trans(NO₃)-dichloro-dinitrato(amcha) platinum (IV) exhibit IR absorption peaks at 1500 cm$^{-1}$, 1300 cm$^{-1}$ and 950 cm$^{-1}$ due to $\nu NO_3$, as shown in FIG. 4 of the attached drawing.

Figure 6:
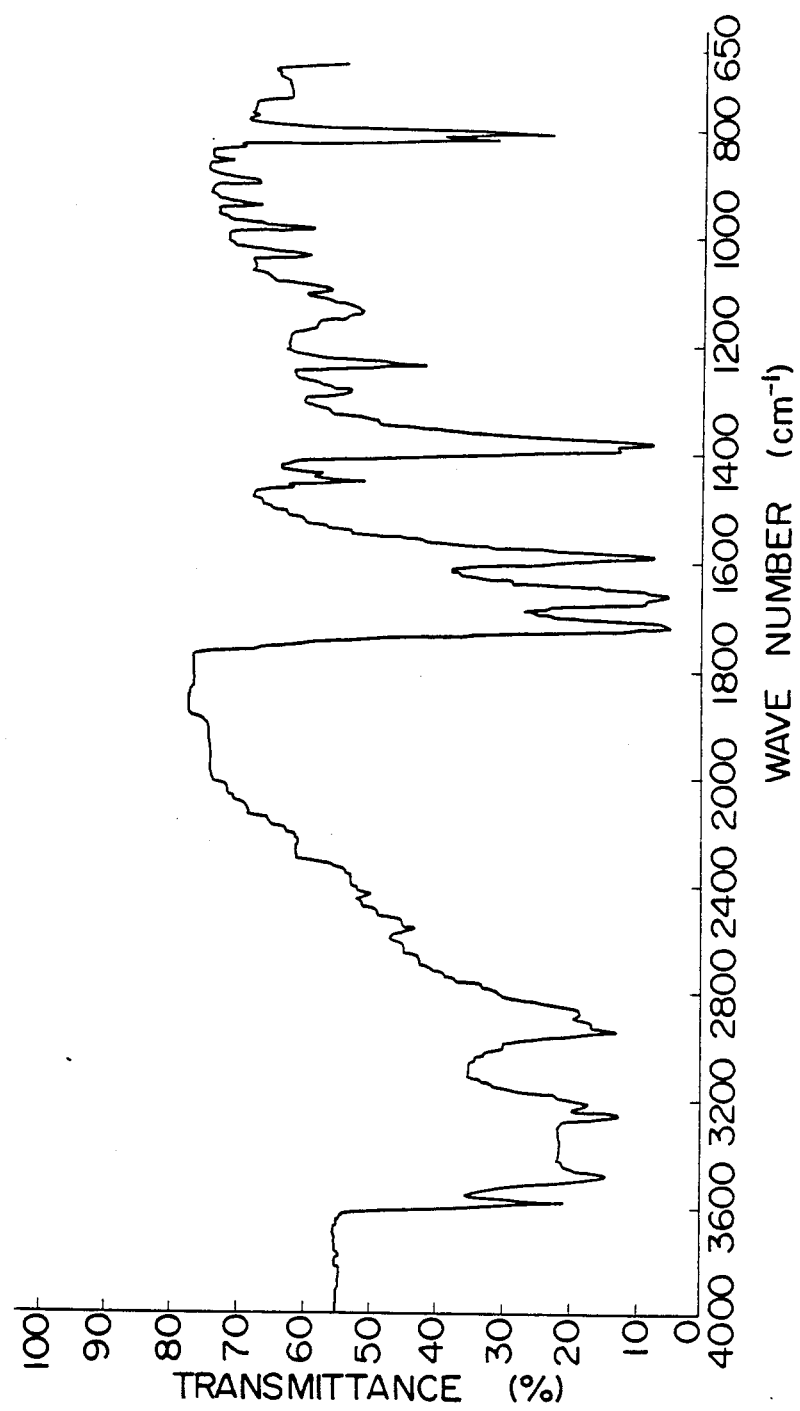
FIG. 6 is infrared absorption spectrum (KBr) of trans(OH)-oxalato-dihydroxo(cis-dach) platinum (IV) according to this invention.
Figure 7:
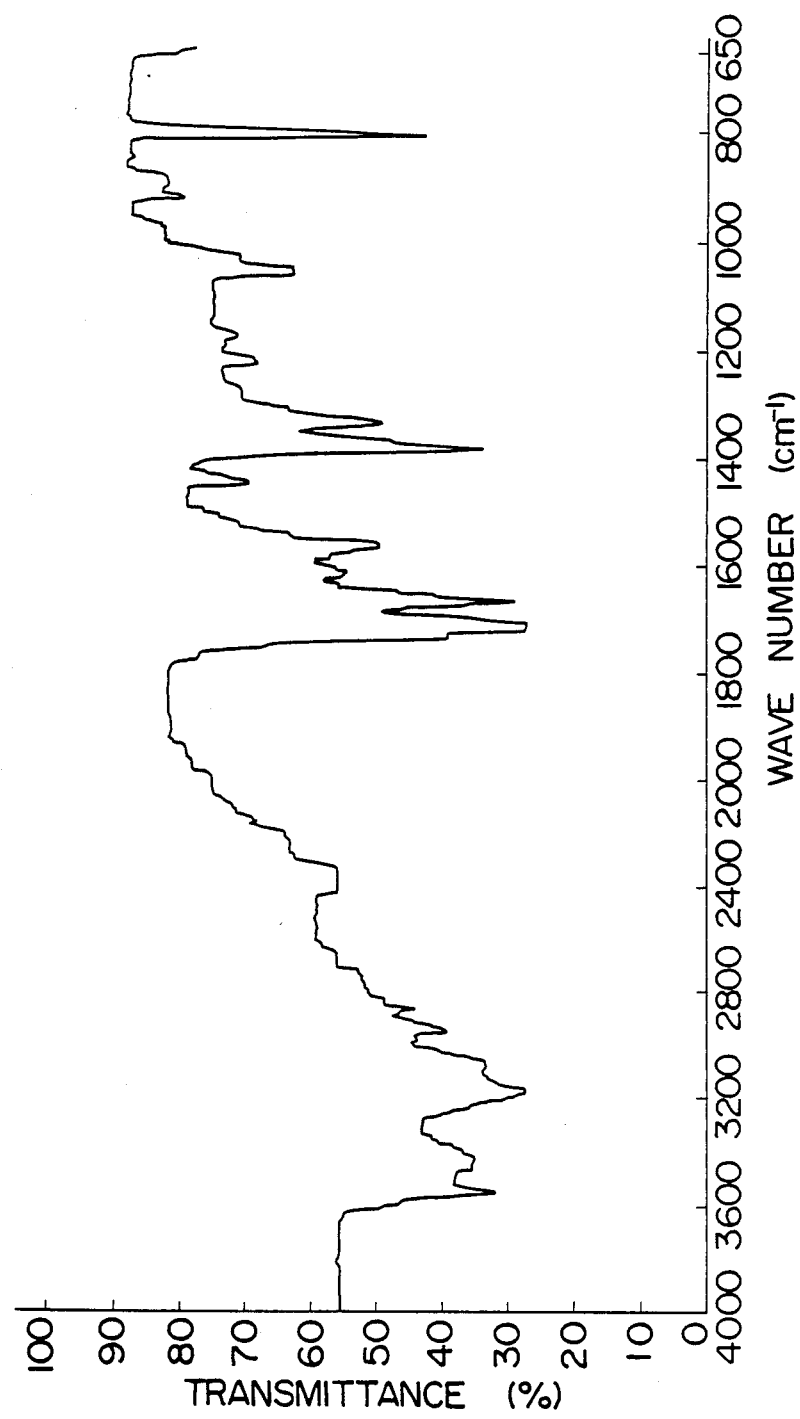
FIG. 7 is infrared absorption spectrum (KBr) of trans(OH)-oxalato-dihydroxo(trans-l-dach) platinum (IV) according to this invention.
Figure 15:
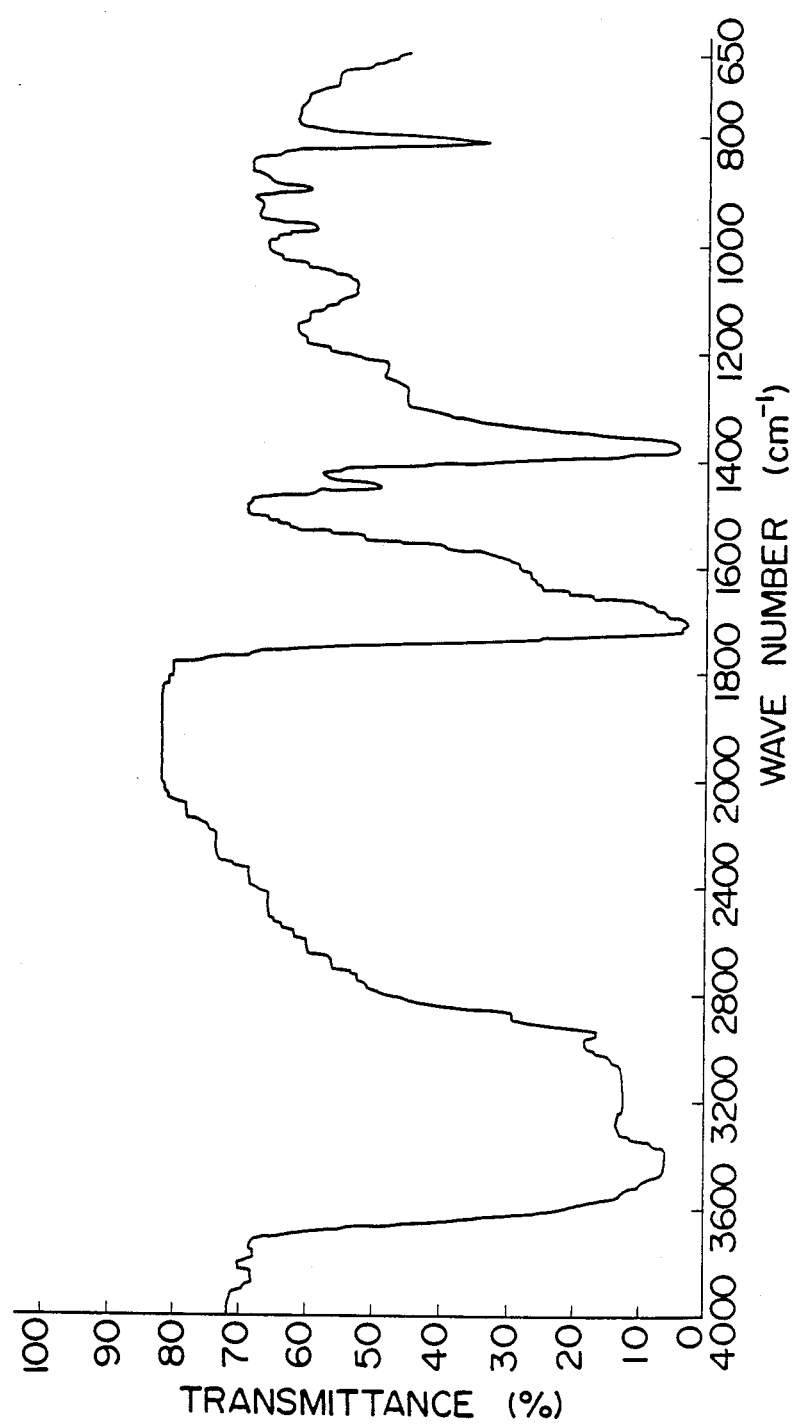
FIG. 15 is infrared absorption spectrum (KBr) of trans(OH)-oxalato-dihydroxo(cis-dl-amcha) platinum (IV) according to this invention.

Trans(OH)-oxalato-dihydroxo(dach) platinum (IV) and trans(OH)-oxalato-dihydroxo(amcha) platinum (IV) exhibit an IR absorption peak at 3500 cm$^{-1}$ due to $\nu OH$, and exhibit strong absorption peaks at 1700 cm$^{-1}$ and 1400 cm$^{-1}$, due to $\nu C=O$ and $\nu C-O$, as shown in FIG. 6, FIG. 7 and FIG. 15.

Figure 8:
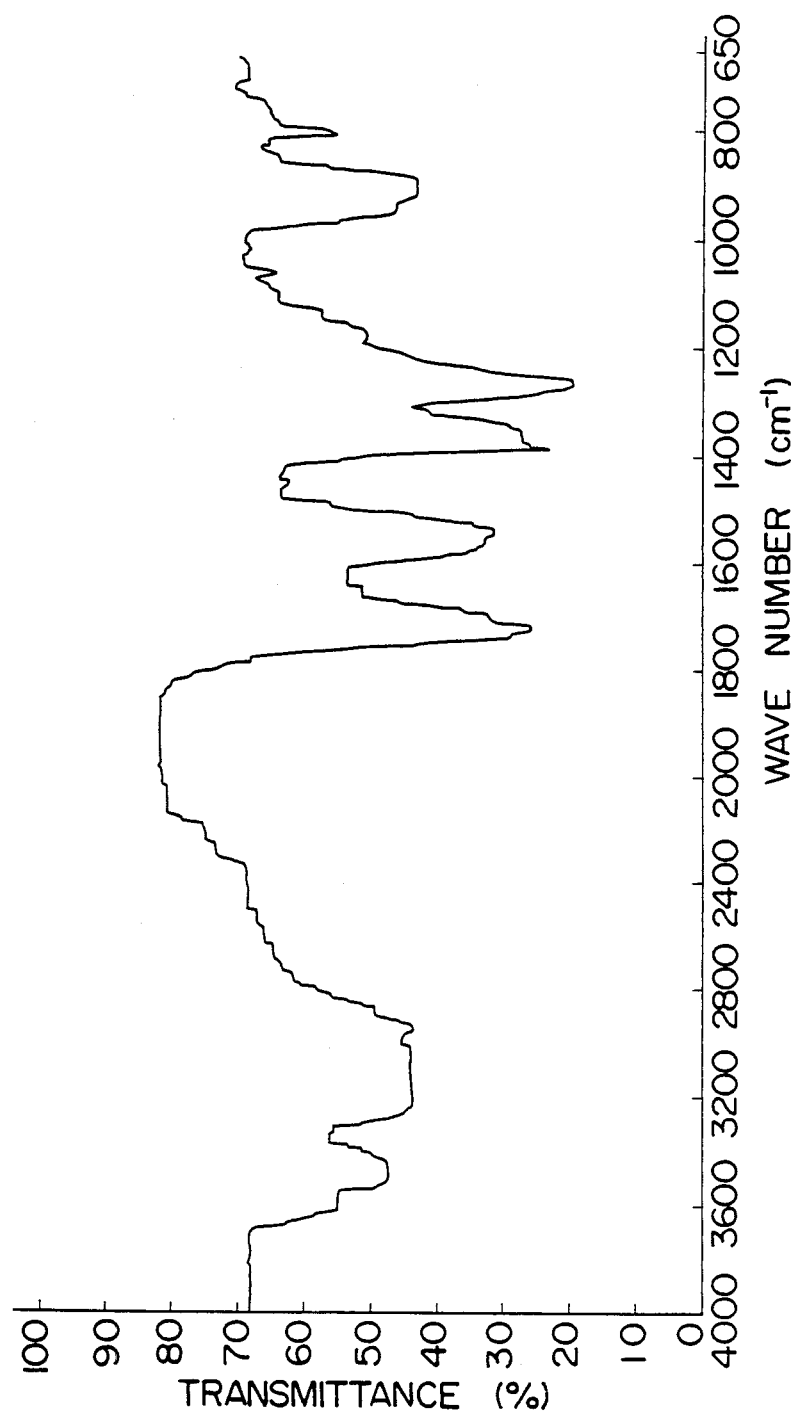
FIG. 8 is infrared absorption spectrum (KBr) of trans($NO_3$)-oxalato-dinitrato(trans-l-dach) platinum (IV) according to this invention.
Figure 16:
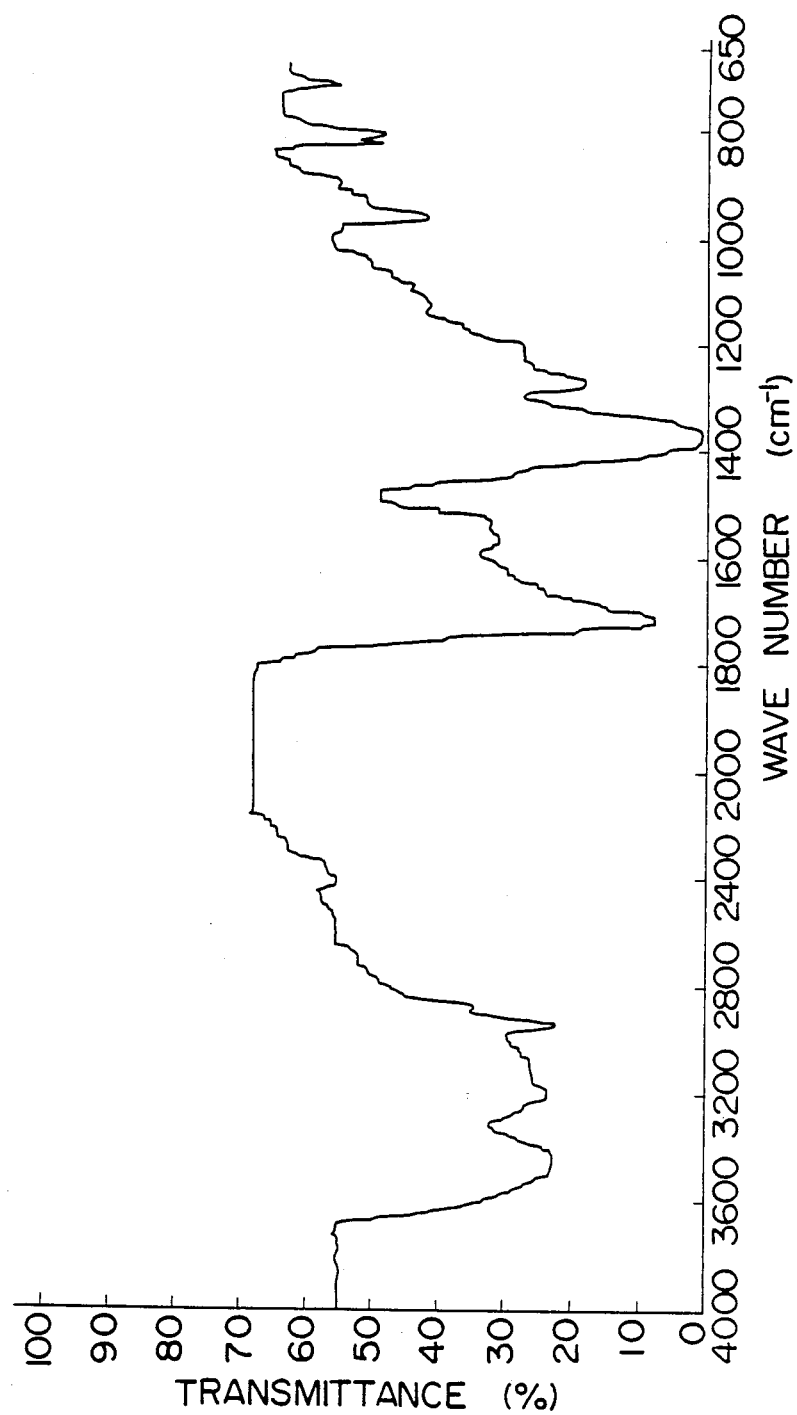
FIG. 16 is infrared absorption spectrum (KBr) of trans($NO_3$)-oxalato-dinitrato(cis-dl-amcha) platinum (IV) according to this invention.
Figure 17:
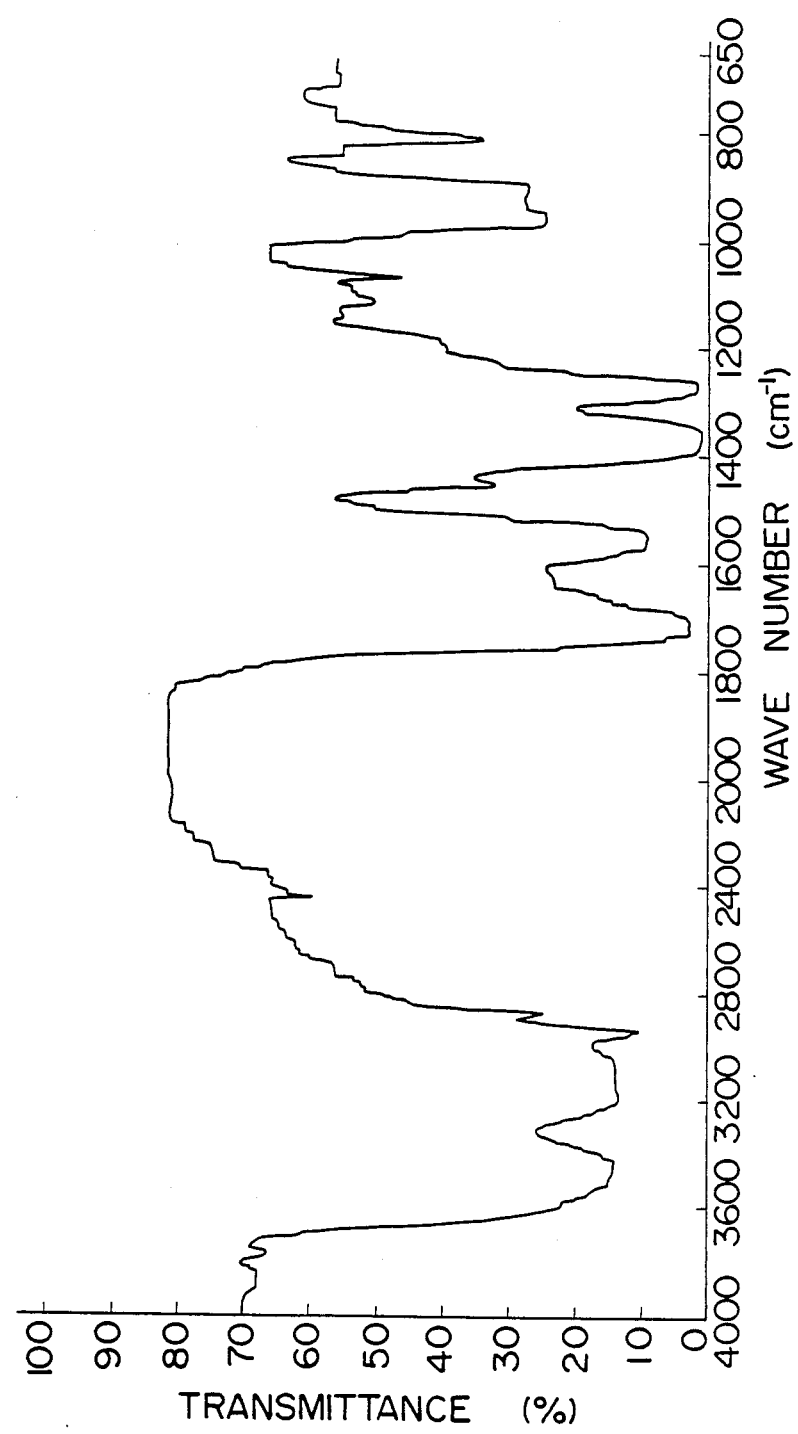
FIG. 17 is infrared absorption spectrum (KBr) of trans($NO_3$)-oxalato-dinitrato(trans-dl-amcha) platinum (IV) according to this invention.

Trans(NO₃)-oxalato-dinitrato(dach) platinum (IV) and trans(NO₃)-oxalato-dinitrato(amcha) platinum (IV), as shown in FIG. 8, FIG. 16 and FIG. 17 of the attached drawing, exhibit IR absorption peaks at 1600 cm$^{-1}$ and 1400 cm$^{-1}$ due to $\nu C=O$ and $\nu C-O$ and IR absorption peaks at 1550 cm$^{-1}$, 1280 cm$^{-1}$ and 950 cm$^{-1}$ due to $\nu NO_3$.

Figure 9:
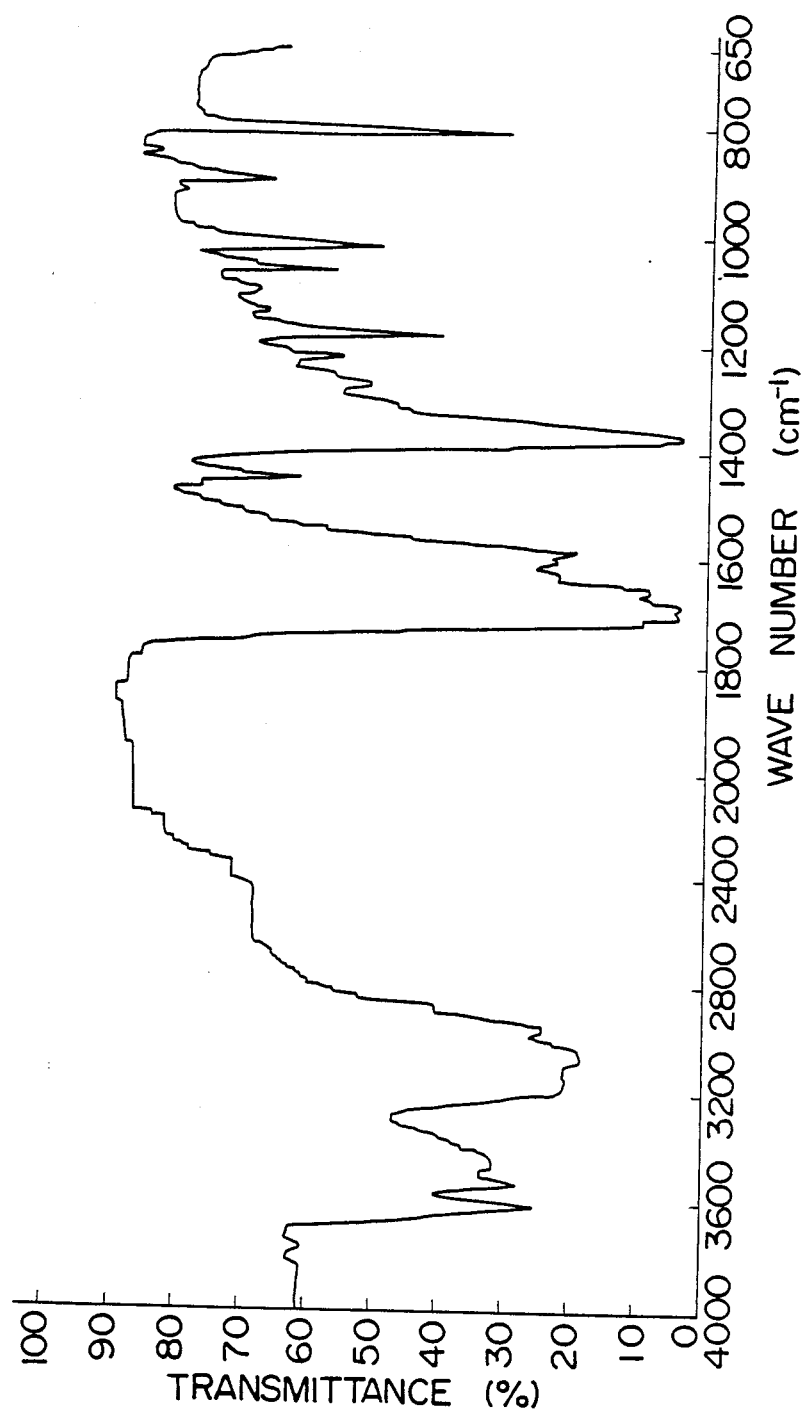
FIG. 9 is infrared absorption spectrum (KBr) of trans(Cl)-oxalato-dichloro(trans-l-dach) platinum (IV) according to this invention.
Figure 10:
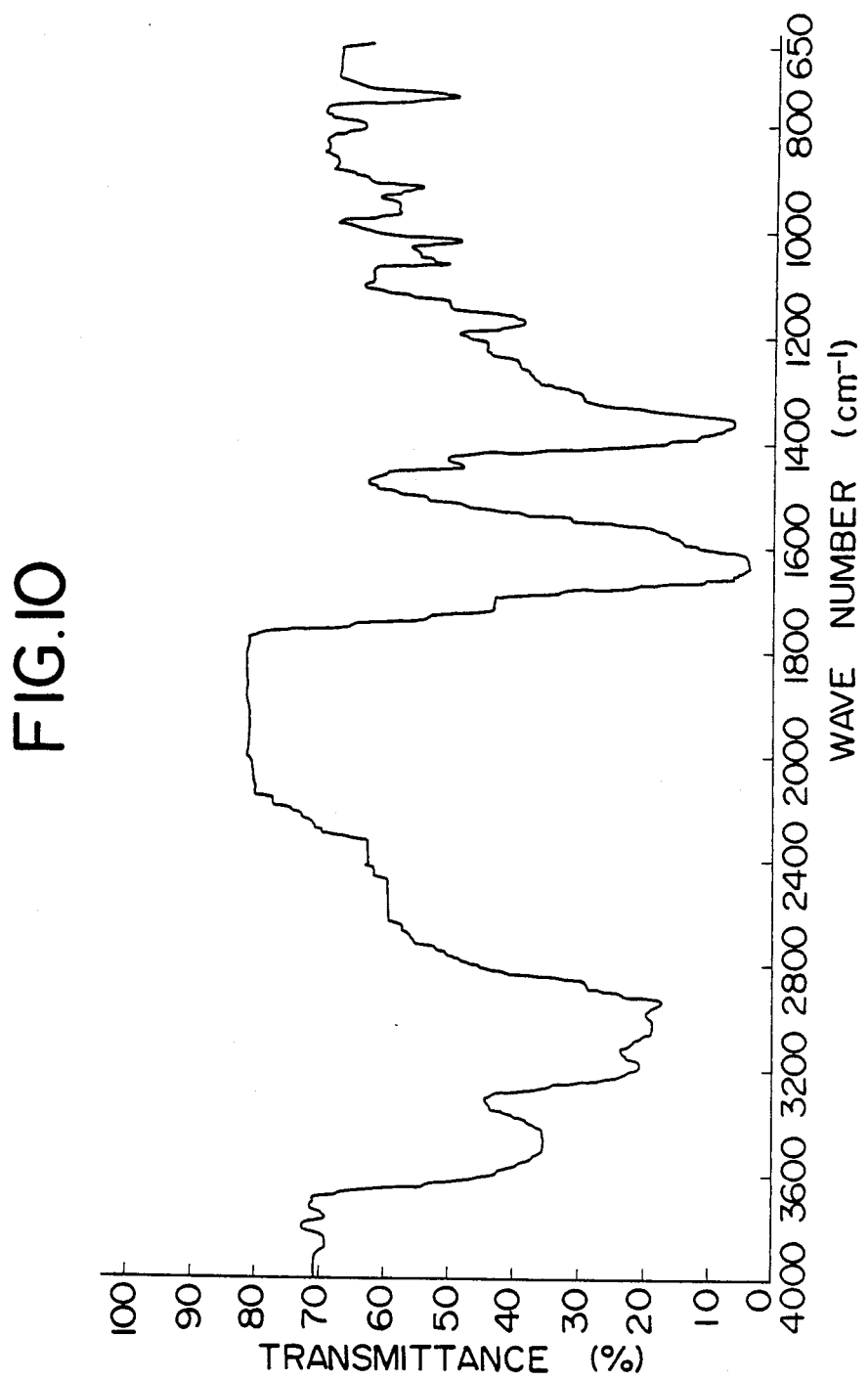
FIG. 10 is infrared absorption spectrum (KBr) of trans(Cl)-malonato-dichloro(trans-l-dach) platinum (IV) according to this invention.
Figure 11:
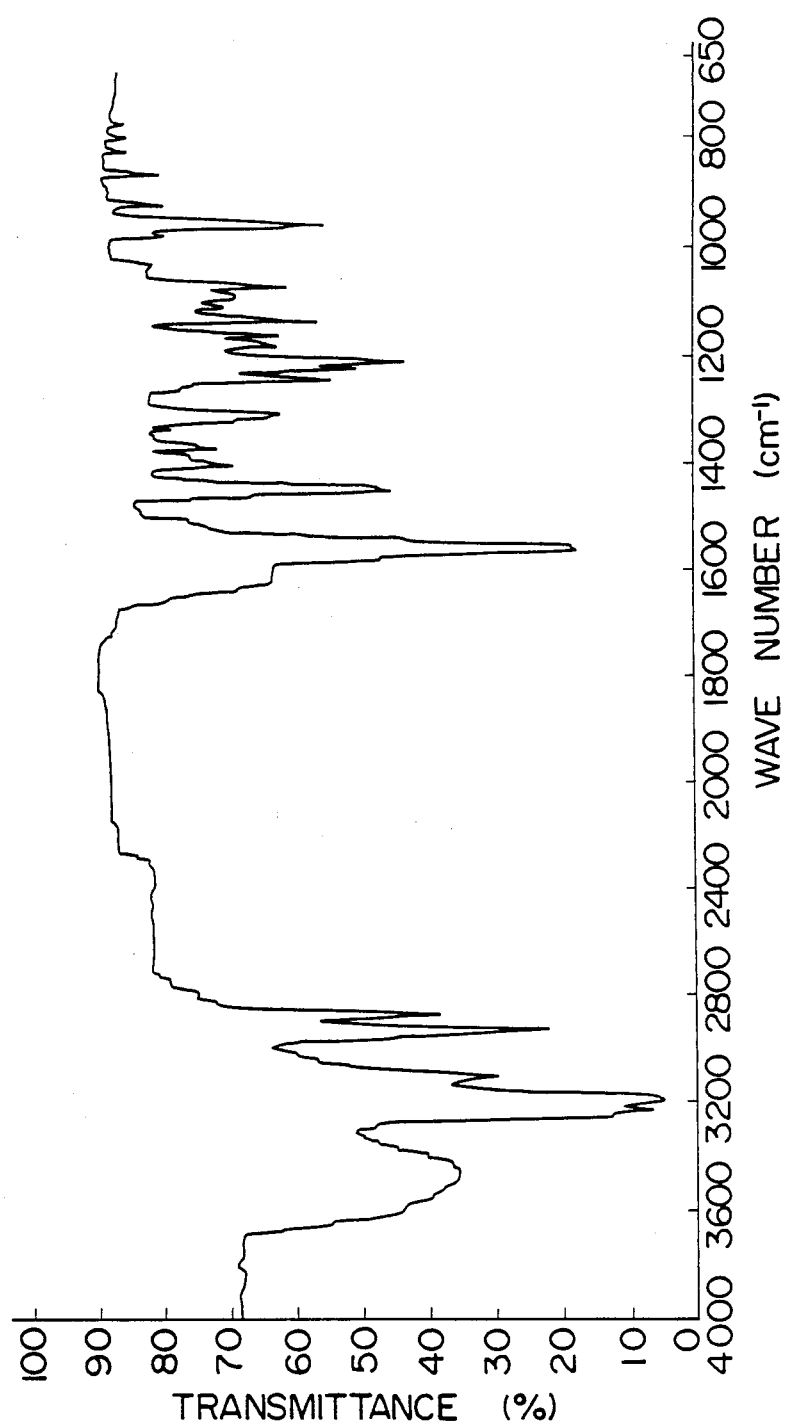
FIG. 11 is infrared absorption spectrum (KBr) of tetrachloro(cis-dl-amcha) platinum (IV) according to this invention.
Figure 12:
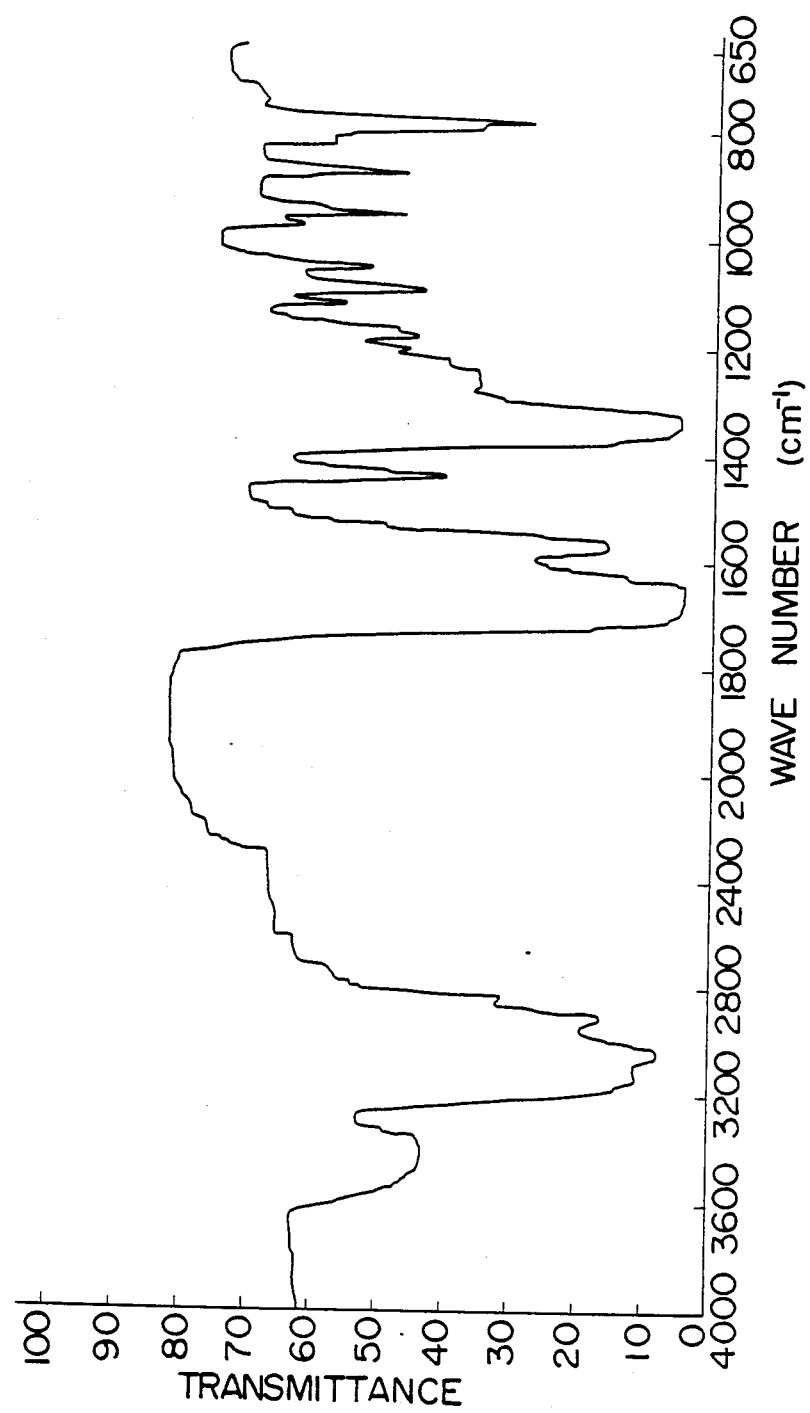
FIG. 12 is infrared absorption spectrum (KBr) of tetrachloro(trans-dl-amcha) platinum (IV) according to this invention.
Figure 18:
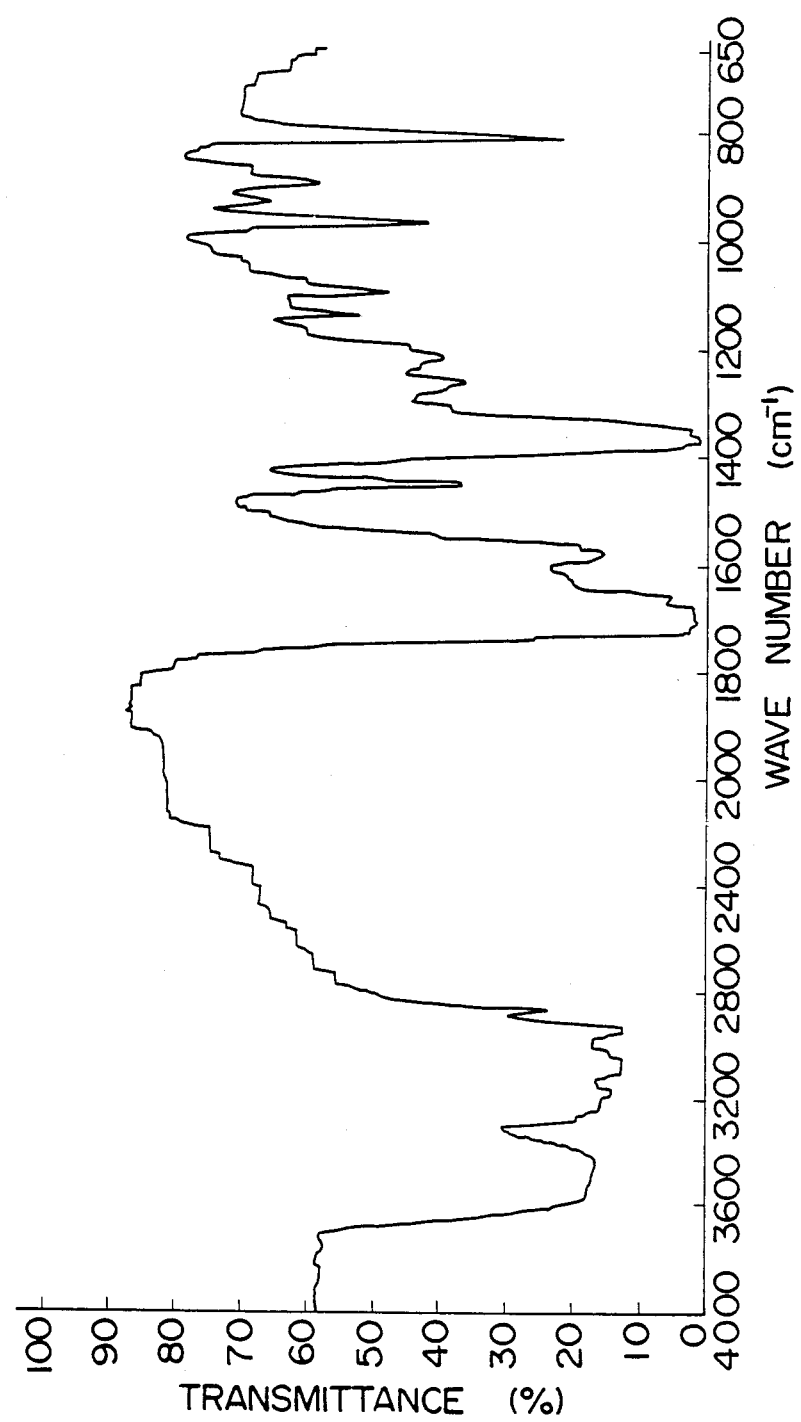
FIG. 18 is infrared absorption spectrum (KBr) of trans(Cl)-oxalato-dichloro(cis-d(-amcha) platinum (IV) according to this invention.

Trans(Cl)-oxalato-dichloro(dach) platinum (IV) and trans(Cl)-oxalato-dichloro(amcha) platinum (IV) exhibit IR absorption peaks at 1700 cm$^{-1}$ and 1380 cm$^{-1}$ due to $\nu C=O$ and $\nu C-O$, as shown in FIG. 9 and FIG. 18 of the attached drawings.

The new platinum (IV) complexes according to this invention exhibit anti-tumor activity against experimental tumors on mouse, such as L1210, P388 and S180A (ascites-tumor), and therefore are useful in chemotherapeutics of tumors. The new platinum (IV) complexes of this invention can be administered orally, intramuscularly or intravenously. They can be formulated into capsules, powders, pellets or injections.

Suitable dosage of the platinum (IV) complexes of this invention is about 1 to 400 mg/kg/day.

The production of the novel platinum (IV) complexes of the formula (I) according to this invention is now illustrated with reference to the following examples. The data of elementary analysis and yield of the organoplatinum (IV) complex as produced in the Examples are listed in Table 1 hereinafter. Compound Numbers given in Table 1 are corresponding to the Example Nos. in which the compound indicated was prepared.

EXAMPLE 1

Preparation of tetrachloro-(cis-dach) platinum (IV)

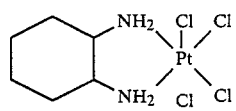

Dichloro-(cis-dach) platinum (II) (1.5) (Compound No. 1 of U.S. Pat. No. 4,169,846) was suspended in water (10 ml), and chlorine gas was passed into the resulting aqueous suspension for 40 minutes at 80° C. on a water bath under stirring and heating. A transparent yellowish reaction solution was thus formed. The reaction solution was passed through with air stream for 5 minutes to remove the remaining chlorine gas therefrom and then the solution was ice-cooled to deposit a precipitate which was then recovered by filtration. Recrystallization of the precipitate from 0.1N aqueous HCl gave a yellowish colored precipitate of the titled complex.

EXAMPLE 2

Preparation of tetrachloro(trans-d-dach) platinum (IV)

Dichloro(trans-d-dach) platinum (IV) as a starting material was reacted with chlorine gas and then processed in the same manner as in Example 1 above, to afford the titled complex.

EXAMPLE 3

Preparation of tetrachloro(trans-l-dach) platinum (IV)

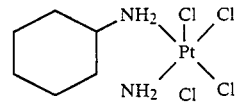

Dichloro(trans-l-dach) platinum (II) as a starting material was reacted with chlorine gas and then processed in the same manner as in Example 1 to afford the titled complex.

EXAMPLE 4

Preparation of trans(OH)-dichloro-dihydroxo-(cis-dach) platinum (IV)

Dichloro(cis-dach) platinum (II) (0.5 g) was suspended in water (10 ml), to which was then added in small portions 30% aqueous hydrogen peroxide (5 ml) at about 70° C. on a water bath under stirring and heating. The resulting suspension was further stirred at 70° C. for 1 hour and allowed to stand so that a transparent reaction solution was formed. The reaction solution was ice-cooled to deposit a precipitate, and this precipitate was then recovered by filtration, washed with a small volume of ethanol and dried under reduced pressure. The titled complex was thus obtained.

EXAMPLE 5

Preparation of trans(OH)-dichloro-dihydroxo(trans-d-dach) platinum (IV)

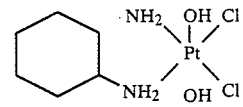

Dichloro(trans-d-dach) platinum (II) as a starting material was reacted with aqueous hydrogen peroxide and then processed in the same manner as in Example 4 above, to afford the titled complex.

EXAMPLE 6

Preparation of trans(OH)-dichloro-dihydroxo(trans-l-dach) platinum (IV)

Dichloro(trans-l-dach) platinum (II) as a starting material was reacted with aqueous hydrogen peroxide and then processed in the same manner as in Example 4 to afford the titled complex.

EXAMPLE 7

Preparation of trans(NO₃)-dichloro-dinitrato(cis-dach) platinum (IV)

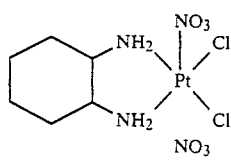

Trans(OH)-dichloro-dihydroxo(cis-dach) platinum (IV) (0.5 g) was suspended in water (10 ml), to which was then added 0.0980N aqueous nitric acid (25 ml). The resulting suspension was stirred at room temperature for 1 hour and allowed to stand for a while. As unreacted substances were remaining, the suspension was further stirred after adding in small portions 0.1N aqueous nitric acid. Thus, a transparent reaction solution was formed. The reaction solution was concentrated under reduced pressure. The resulting solid residue was washed with a small volume of ethanol and dried under reduced pressure, to afford the titled complex.

EXAMPLE 8

Preparation of trans(NO₃)-dinitrato-dichloro(trans-d-dach) platinum (IV)

Trans(OH)-dichloro-dihydroxo(trans-d-dach) platinum (IV) as a starting material was reacted with aqueous nitric acid and then processed in the same manner as in Example 8 above, to afford the titled complex.

EXAMPLE 9

Preparation of trans(NO₃)-dinitrato-dichloro(trans-l-dach) platinum (IV)

Trans(OH)-dichloro-dihydroxo(trans-l-dach) platinum (IV) as a starting material was reacted with aqueous nitric acid and processed in the same manner as in Example 8, to afford the titled complex.

EXAMPLE 10

Preparation of trans(OH)-oxalato-dihydroxo(cis-dach) platinum (IV)

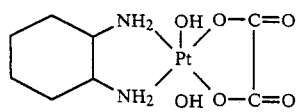

Oxalato-(cis-dach) platinum (II) (0.5 g) (Compound No. 4 of U.S. Pat. No. 4,169,846) was suspended in water (10 ml), to which was then added in small portions 30% aqueous hydrogen peroxide (5 ml) at 70° C. on a water bath under stirring and heating, followed by stirring at the same temperature for further 1 hour. Thus, a transparent reaction solution was formed. The reaction solution was ice-cooled to deposit a precipitate, and this solid was recovered by filtration, washed with a small volume of ethanol and dried under reduced pressure, to afford the titled complex.

EXAMPLE 11

Preparation of trans(OH)-oxalato-dihydroxo(trans-d-dach) platinum (IV)

Oxalato-(trans-d-dach) platinum (II) as a starting material was reacted with aqueous hydrogen peroxide and then processed in the same manner as in Example 10 above, to afford the titled complex.

EXAMPLE 12

Preparation of trans(OH)-oxalato-dihydroxo(trans-l-dach) platinum (IV)

Oxalato-(trans-l-dach) platinum (II) as a starting material was reacted with aqueous hydrogen peroxide and then processed in the same manner as in Example 10, to afford the titled complex.

EXAMPLE 13

Preparation of trans(NO₃)-oxalato-dinitrato(cis-dach) platinum (IV)

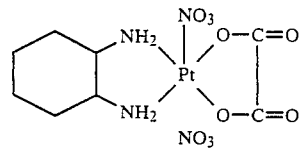

Trans(OH)-oxalato-dihydroxo(cis-dach) platinum (IV) (0.3 g) was suspended in water (10 ml), to which was then added 0.0980N aqueous nitric acid (7.1 ml). The suspension obtained was stirred at room temperature for 3 hours and allowed to stand until a transparent reaction solution was formed. This solution was ice-cooled to deposit a precipitate, and the precipitate was recovered by filtration, washed with a small volume of ethanol and dried under reduced pressure, to afford the titled complex.

EXAMPLE 14

Preparation of trans(NO₃)-oxalato-dinitrato(trans-d-dach) platinum (IV)

Trans(OH)-oxalato-dihydroxo(trans-d-dach) platinum (IV) as a starting material was reacted with aqueous nitric acid and processed in the same manner as in Example 13 above, to afford the titled complex.

EXAMPLE 15

Preparation of trans(NO₃)-oxalato-dinitrato(trans-L-dach) platinum (IV)

Trans(OH)-oxalato-dihydroxo(trans-l-dach) platinum (IV) as a starting material was reacted with aqueous nitric acid and processed in a manner similar to Example 13, to afford the titled complex.

EXAMPLE 16

Preparation of trans(Cl)-oxalato-dichloro(cis-dach) platinum (IV)

Oxalato(cis-dach) platinum (II) (0.5 g) was suspended in water (5 ml), into which was then passed chlorine gas for 45 minutes under heating at 70° C. on a water bath. The resulting suspension was passed through with air stream for 10 minutes to remove the residual chlorine gas therefrom, so that a transparent, yellow colored reaction solution was obtained. The reaction solution was ice-cooled to deposit a precipitate which was then recovered by filtration. The solid product obtained was dried under reduced pressure, to afford the titled complex.

EXAMPLE 17

Preparation of trans(Cl)-oxalato-dichloro(trans-d-dach) platinum (IV)

Oxalato(trans-d-dach) platinum (II) as a starting material was reacted with chlorine gas and then processed in the same manner as in Example 16 above, to afford the titled complex.

EXAMPLE 18

Preparation of trans(Cl)-oxalato-dichloro(trans-l-dach) platinum (IV)

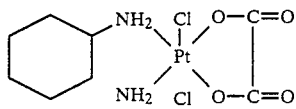

Oxalato (trans-l-dach) platinum (II) as a starting material was reacted with chlorine gas and then processed in the same manner as in Example 16, to afford the titled complex.

EXAMPLE 19

Preparation of trans(OH)-malonato-dihydroxo(cis-dach) platinum (IV)

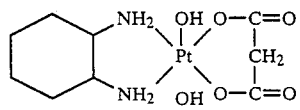

Malonato (cis-dach) platinum (II) (0.5 g) (Compound No. 7 of U.S. Pat. No. 4,169,846) was suspended in water (5 ml), to which was then added 30% aqueous hydrogen peroxide (6.2 ml). The suspension so obtained was stirred at room temperature for 1 hour and allowed to stand until a transparent reaction solution was formed. The reaction solution was concentrated under reduced pressure and the residue was admixed with ethanol to deposit a precipitate which was then recovered by filtration. Recrystallization of the precipitate from a small volume of water gave a crystalline product. This product was dried under reduced pressure to give the titled complex.

EXAMPLE 20

Preparation of trans(OH)-malonato-dihydroxo(trans-d-dach) platinum (IV)

Malonato(trans-d-dach) platinum (II) as a starting material was reacted with aqueous hydrogen peroxide and then processed in the same manner as in Example 19 above, to afford the titled complex.

EXAMPLE 21

Preparation of trans(OH)-malonato-dihydroxo(trans-l-dach) platinum (IV)

Malonato(trans-l-dach) platinum (II) as a starting material was reacted with aqueous hydrogen peroxide and then processed in the same manner as in Example 19, to afford the titled complex.

EXAMPLE 22

Preparation of trans(Cl)-malonato-dichloro(cis-dach) platinum (IV)

Trans(OH)-malonato-dihyroxo(cis-dach) platinum (IV) (0.54 g) was suspended in water (20 ml), to which was then added 0.100N aqueous hydrochloric acid (24 ml). The resulting suspension was stirred at room temperature for 30 minutes and allowed to stand until a transparent reaction solution was formed. The reaction solution was concentrated and the residue was dried under reduced pressure. The dried residue was dissolved in ethanol (30 ml) at 50° C. and the solution was filtrated to remove a small amount of colorless, insoluble matter. The filtrate was concentrated and dried under reduced pressure, and a yellow solid residue obtained was washed with a small volume of ethanol and dried, to afford the titled complex.

EXAMPLE 23

Preparation of trans(Cl)-malonato-dichloro(trans-d-dach) platinum (IV)

Trans(OH)-malonato-dihydroxo(trans-d-dach) platinum (IV) as a starting material was reacted with hydrochloric acid and then processed in the same manner as in Example 22 above, to afford the titled complex.

EXAMPLE 24

Preparation of trans(Cl)-malonato-dichloro(trans-l-dach) platinum (IV)

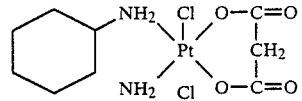

Trans(OH)-malonato-dihydroxo(trans-l-dach) platinum (IV) as a starting material was reacted with aqueous hydrochloric acid and then processed in the same manner as in Example 22, to afford the titled complex.

EXAMPLE 25

Preparation of tetrachloro(cis-dl-amcha) platinum (IV)

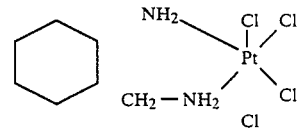

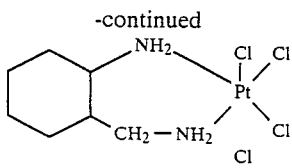

Dichloro(cis-dl-amcha) platinum (II) (0.5 g) (see U.S. Pat. No. 4,255 347) was suspended in water (5 ml), into which was then passed chlorine gas for 45 minutes under heating at 70° C. on a water bath. The resulting suspension was passed through with air stream for 10 minutes to remove the remaining chlorine gas therefrom. The resultant yellow and transparent reaction solution was ice-cooled to deposit a precipitate, and this precipitate was recovered by filtration and dried under reduced pressure, to afford the titled complex.

EXAMPLE 26

Preparation of tetrachloro(trans-dl-amcha) platinum (IV)

Dichloro(trans-dl-amcha) platinum (IV) as a starting material was reacted with chlorine gas and then processed in the same manner as in Example 25 above, to afford the titled complex.

EXAMPLE 27

Preparation of trans(OH)-dichloro-dihydroxo(cis-dl-amcha) platinum (IV)

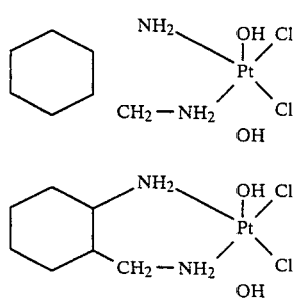

Dichloro(cis-dl-amcha) platinum (II) (0.5 g) was suspended in water (5 ml), to which was then added 30% aqueous hydrogen peroxide (25 ml) under heating at 70° C. on a water bath. The resulting suspension was stirred for 45 minutes and allowed to stand. The resultant transparent and yellow reaction solution was concentrated to 3 ml under reduced pressure. The concentrate was admixed with ethanol to deposit a precipitate which was recovered by filtration. The titled complex was thus obtained.

EXAMPLE 28

Preparation of trans(OH)-dichloro-dihydroxo(trans-dl-amcha) platinum (IV)

Dichloro(trans-dl-amcha) platinum (II) as a starting material was reacted with aqueous hydrogen peroxide and then processed in the same manner as in Example 27 above, to afford the titled complex.

EXAMPLE 29

Preparation of trans(NO₃)-dichloro-dinitrato(cis-dl-amcha) platinum (IV)

Trans(OH)-dichloro-dihydroxo(cis-dl-amcha) platinum (IV) (0.5 g) was suspended in water (5 ml), to which was then added 0.1 N aqueous nitric acid (25 ml). The resulting suspension was stirred at room temperature for 1 hour to effect the reaction. The resultant transparent reaction solution was concentrated under reduced pressure. The solid residue was washed with a small volume of ethanol and dried under reduced pressure, to obtain the titled complex.

EXAMPLE 30

Preparation of trans(NO₃)-dichloro-dinitrato(trans-dl-amcha) platinum (IV)

Trans(OH)-dichloro-dihydroxo(trans-dl-amcha) platinum (IV) as a starting material was reacted with aqueous nitric acid and then processed in the same manner as in Example 29 above, to afford the titled complex.

EXAMPLE 31

Preparation of trans(OH)-oxalato-dihydroxo(cis-dl-amcha) platinum (IV)

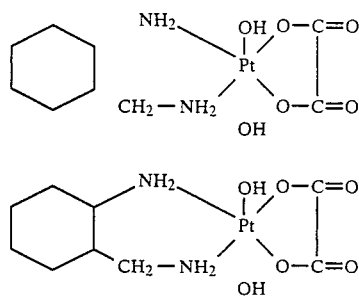

Oxalato(cis-dl-amcha) platinum (II) (1.0 g) (see U.S. Pat. No. 4,255,347) was suspended in water (10 ml), to which was then added 30% aqueous hydrogen peroxide (50 ml) under heating at 70° C. on a water bath, and the resulting suspension was further stirred for 45 minutes to effect the reaction. The resultant clear reaction solution was concentrated to 5 ml under reduced pressure. The concentrate was admixed with ethanol to deposit a colorless precipitate. This precipitate was recovered by filtration and dried under reduced pressure, to afford the titled complex.

EXAMPLE 32

Preparation of trans(OH)-oxalato-dihydroxo(trans-dl-amcha) platinum (IV)

Oxalato(trans-dl-amcha) platinum (II) as a starting material was reacted with aqueous hydrogen peroxide and then processed in the same manner as in Example 31 above, to afford the titled complex.

EXAMPLE 33

Preparation of trans(NO₃)-oxalato-dinitrato(cis-dl-amcha) platinum (IV)

Trans(OH)-oxalato-dihydroxo(cis-dl-amcha) platinum (IV) (1.0 g) was suspended in water (10 mg), to which was then added 0.1N aqueous nitric acid (50 ml), and the resulting suspension was further stirred at room temperature for 1 hour to effect the reaction. The resultant reaction solution was concentrated under reduced pressure. The concentrate was washed with a small volume of ethanol and dried under reduced pressure, to afford the titled complex.

EXAMPLE 34

Preparation of trans(NO₃)-oxalato-nitrato(trans-dl-amcha) platinum (IV)

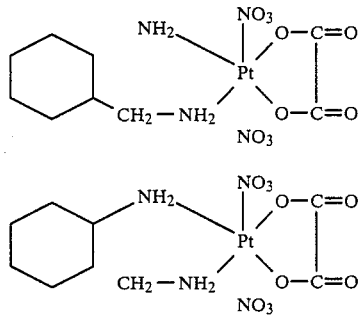

Trans(OH)-oxalato-dihydroxo(trans-dl-amcha) platinum (IV) as a starting material was reacted with aqueous nitric acid and then processed the same manner as in Example 33 above, to afford the titled complex.

EXAMPLE 35

Preparation of trans(Cl)-oxalato-dichloro(cis-dl-amcha) platinum (IV)

Oxalato(cis-dl-amcha) platinum (II) (1.0 g) was suspended in water (10 ml), into which was then passed chlorine gas for 1 hour under heating at 70° C. on a water bath. The resulting suspension was passed through with air stream for 10 minutes to remove the remaining chlorine gas therefrom. The resultant clear and yellow reaction solution was ice-cooled to deposit a precipitate, and the precipitate was recovered by filtration and dried under reduced pressure, to afford the titled complex.

EXAMPLE 36

Preparation of trans(Cl)-oxalato-dichloro(trans-dl-amcha) platinum (IV)

Oxalato(trans-dl-amcha) platinum (IV) as a starting material was reacted with chlorine gas and then processed in a manner similar to Example 35, to afford the titled complex.

The elementary analysis value and the yield of the respective platinum (IV) complex according to this invention as obtained in the Examples 1 to 36 above, are summarized in Table 1 below.

TABLE 1

| Compound No. (Example No.) | Found value (%) | | | Calculated value (%) | | | Yield (%) |
|---|---|---|---|---|---|---|---|
| | H | O | N | H | O | N | |
| 1 | 3.08 | 16.22 | 6.23 | | | | 53 |
| 2 | 3.09 | 15.89 | 6.06 | 3.10 | 16.96 | 6.21 | 58 |
| 3 | 3.11 | 15.79 | 6.23 | | | | 70 |
| 4 | 3.88 | 17.31 | 6.64 | | | | 76 |
| 5 | 3.76 | 17.40 | 6.89 | 3.86 | 17.39 | 6.76 | 75 |
| 6 | 3.71 | 17.40 | 6.51 | | | | 80 |
| 7 | 2.85 | 14.12 | 10.98 | 2.73 | 14.30 | 11.08 | 80 |
| 8 | 2.80 | 14.30 | 11.11 | | | | 75 |
| 9 (½-hydrate) | 2.91 | 13.79 | 10.87 | 2.95 | 14.05 | 10.92 | 80 |
| 10 | 3.84 | 21.79 | 6.38 | | | | 85 |
| 11 | 3.54 | 22.05 | 6.22 | 3.74 | 22.28 | 6.50 | 80 |
| 12 | 3.72 | 22.16 | 6.49 | | | | 85 |
| 13 (di-hydrate) | 3.20 | 17.42 | 9.70 | 3.24 | 17.33 | 9.98 | 85 |
| 14 (di-hydrate) | 3.26 | 17.42 | 10.05 | 3.24 | 17.33 | 9.98 | 75 |
| 15 (3/2-hydrate) | 3.13 | 17.53 | 10.22 | 3.18 | 17.62 | 9.88 | 70 |
| 16 | 2.87 | 20.37 | 6.24 | | | | 70 |
| 17 | 3.14 | 20.43 | 6.28 | 3.00 | 20.56 | 6.13 | 68 |
| 18 | 3.12 | 20.45 | 6.02 | | | | 72 |
| 19 | 3.92 | 24.15 | 6.18 | 4.04 | 24.27 | 6.29 | 70 |
| 20 | 4.28 | 24.35 | 6.35 | | | | 80 |
| 21 (3/2-hydrate) | 4.12 | 22.71 | 6.07 | 4.48 | 22.88 | 5.93 | 88 |
| 22 | 3.29 | 22.35 | 5.73 | 3.32 | 22.41 | 5.81 | 70 |
| 23 | 3.42 | 22.52 | 5.92 | | | | 75 |
| 24 (½-hydrate) | 3.85 | 21.99 | 5.44 | 3.88 | 21.92 | 5.68 | 80 |
| 25 | 3.22 | 18.42 | 5.99 | 3.45 | 18.14 | 6.05 | 70 |
| 26 | 3.42 | 18.33 | 5.99 | | | 6.65 | |
| 27 | 4.59 | 19.93 | 6.40 | 4.22 | 19.67 | 6.56 | 52 |
| 28 | 3.96 | 19.63 | 6.39 | | | 6.50 | |
| 29 | 3.21 | 16.05 | 10.63 | 3.09 | 16.22 | 10.81 | 75 |
| 30 | 3.15 | 16.32 | 10.92 | | | | 70 |
| 31 (mono-hydrate) | 4.22 | 22.95 | 6.11 | 4.32 | 23.32 | 6.05 | 63 |

TABLE 1-continued

| Compound No. (Example No.) | Found value (%) H | O | N | Calculated value (%) H | O | N | Yield (%) |
|---|---|---|---|---|---|---|---|
| 32 | 4.03 | 24.10 | 6.27 | 4.04 | 24.27 | 6.29 | 47 |
| 33 | 3.48 | 18.73 | 10.27 | 2.99 | 20.19 | 10.47 | 40 |
| 34 (di-hydrate) | 3.36 | 18.67 | 10.12 | 3.50 | 18.91 | 9.81 | 35 |
| 35 (tri-hydrate) | 3.42 | 21.21 | 5.33 | 3.61 | 21.64 | 5.61 | 63 |
| 36 | 3.66 | 22.16 | 5.57 | 3.33 | 22.45 | 5.82 | 81 |

EXPERIMENT 1

Anti-tumor activity of the platinum (IV) complex of this invention on mice against Leukemia L-1210 is now estimated.

To test the anti-tumor activity of the platinum (IV) complexes according to this invention, 10⁵ cells/mouse of Leukemia L-1210 were transplanted by intraperitoneal injection to groups (6 mice in each group) of CDF mice. On the same day of the transplantation, and 5 days and 9 days after the transplantation of Leukemia L-1210 cells, the platinum (IV) complex under test was administered by intraperitoneal injection to the test mice. The antitumor activity of the test platinum (IV) complex was evaluated by means of rate (%) of prolongation of mean survival days of the treated mice, in term of the values of T/C %, i.e., the value of 100 times the mean survival period of the groups of mice treated with the test platinum complex, divided by the mean survival period of the comparative groups of mice which were not treated with the test platinum complex. The test results are as shown in Table 2 below. In Table 2, the T/C (%) values of higher than 125% (the numerical value as underlined) means that the tested platinum complex has a substantial anti-tumor activity.

In Table 2, the numerical figure given in parenthesis denotes the number of the mice as entirely cured in each group of mice treated. The term "T" denotes that the incurred decrease in body weight of the treated mice exceeded the lowest limit value (−4 g) for judgement of the toxic effects of the test compound. The test results shown in Table 2 demonstrates that the platinum (IV) complexes of this invention have a significant anti-tumor activity.

TABLE 2

| Compound No. of platinum (IV) complex | Rate (%) of prolongation of mean survival period (T/C, %) Dose (mg/kg) | | | | | | | | |
|---|---|---|---|---|---|---|---|---|---|
| | 400 | 200 | 100 | 50 | 25 | 12.5 | 6.25 | 3.12 | 1.56 |
| 1 | | | | | | | 202(1) | 124 | 121 |
| 2 | | | | | | | 179 | 143 | 143 |
| 3 | | | | | | | 307(2) | 256(1) | 147 |
| 4 | | | | 153 | 144 | 125 | | | |
| 5 | | | | "T" 266(2) | 208(1) | 157 | | | |
| 6 | | | | "T" 104 | 382(1) | 209(1) | | | |
| 10 | | | | 114 | 111 | 108 | | | |
| 11 | | | 0 | 106 | 98 | | | | |
| 12 | | | | 119 | 108 | 114 | | | |
| 14 | "T" 81 | "T" 92 | 210 | | 115 | 112 | 101 | | |
| 15 | | | | | 217 | 156 | 121 | | |
| 18 | | | | 153 | 350(3) | 311(3) | | | |
| 21 | | | 106 | 100 | 114 | | | | |
| 24 | | | 0 | 243(2) | 286(2) | | | | |
| 25 | | | | | | 224(1) | 153 | 192(1) | |
| 26 | | | | "T" 256(1) | 300(3) | 217(1) | 170 | 124 | 111 |
| 27 | | | | 211 | 212 | 132 | | | |
| 28 | | | | 147 | 138 | 119 | | | |
| 29 | | | | "T" 75 | "T" 87 | "T" 143 | | | |
| 31 | 245(1) | 221(1) | 181 | 117 | 100 | 102 | | | |
| 32 | 250(1) | 164 | 129 | 117 | 105 | 115 | | | |
| 33 | | | 0 | 75 | 81 | | | | |
| 34 | | | 268(1) | 253(1) | 148 | | | | |
| 35 | | | | 95 | 95 | 176 | | | |
| 36 | | | | 119 | 309(3) | 306(2) | | | |

What we claim is:
1. A platinum (IV) complex represented by the formula (I)

wherein the moiety

denotes a 1,2-cyclohexanediamine ligand of the formula:

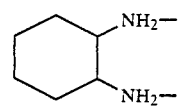

where the 1- and 2-amino groups have a configuration selected from cis-, trans-l, and trans-d- relative to the cyclohexane ring; or the moiety

denotes a 2-(aminomethyl)cyclohexylamine ligand of the formula:

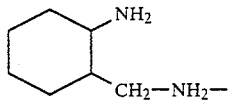

where the 1-amino group and 2-aminomethyl group have a configuration selected from cis-l-, cis-d-, trans-l- and trans-d-, or a mixture thereof relative to the cyclohexane ring, B and B' taken together with the platinum atom form a ring of the formula:

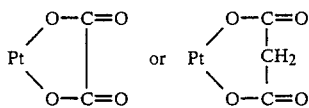

or B and B' are the same and each deontes a chloro group, and D denotes a chloro group, a nitrate group or a hydroxy group with both D groups being the same.

2. A complex of claim 1 in which the moiety

is a ligand selected from cis-1,2-cyclohexanediamine, trans-d-1,2-cyclohexanediamine and trans-l-1,2-cyclohexanediamine, and B, B' and D are each a chloro group.

3. A complex of claim 1 in which the moiety

is a ligand selected from cis-1,2-cyclohexanediamine, trans-d-1,2-cyclohexanediamine and trans-l-1,2-cyclohexanediamine, and B and B' each a chloro group and D is hydroxy group (OH) or nitrate group ($NO_3$).

4. A complex of claim 1 in which the moiety

a ligand selected from cis-1,2-cyclohexanediamine, trans-d-1,2-cyclohexanediamine and trans-1,2-cyclohexanediamine, and B and B' together form a group of the formula

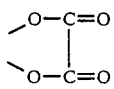

and D is a hydroxyl group OH, a chloro group Cl or a nitrate group $NO_3$.

5. A complex of claim 1 in which the moiety

is a ligand selected from cis-1,2-cyclohexanediamine, trans-d-1,2-cyclohexanediamine and trans-l-1,2-cyclohexane-diamine, and B and B' taken together form a group of the formula

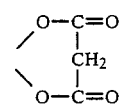

and D is a hydroxy group (OH), a chloro group (Cl) or a nitrate group ($NO_3$).

6. A complex of claim 1 in which the moiety

is a ligand selected from cis-dl-2-(aminomethyl)cyclohexyl-amine and trans-dl-2-(aminomethyl)cyclohexylamine, and B, B' and D are each a chloro group.

7. A complex of claim 1 in which the moiety

is a ligand selected from cis-dl-2-(aminomethyl)cyclohexylamine and trans-dl-2-(aminomethyl)cyclohexylamine, and B and B' are each a chloro group, and D is a hydroxy group (OH) or a nitrate group ($NO_3$).

8. A complex of claim 1 in which the moiety

is a ligand selected from cis-dl-2-(aminomethyl)cyclohexylamine and trans-dl-2-(aminomethyl)cyclohexylamine, and B and B' taken together form a group of the formula

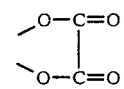

and D is a hydroxy group OH, a chloro group Cl or a nitrate group $NO_3$.

9. Trans (Cl)-oxalato-dichloro(trans-l-dach)-platinum (IV).

* * * * *